(12) United States Patent
Silverman et al.

(10) Patent No.: US 7,470,815 B1
(45) Date of Patent: Dec. 30, 2008

(54) SELECTIVE NEURONAL NITRIC OXIDE SYNTHASE INHIBITORS

(75) Inventors: Richard B. Silverman, Northbrook, IL (US); Jung-Mi Hah, Seoul (KR); Jose Antonio Gomez Vidal, Granada (ES); Erik Erdal, Woodridge, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 11/341,404

(22) Filed: Jan. 26, 2006

(51) Int. Cl.
 *C07C 279/32* (2006.01)

(52) U.S. Cl. ..................................................... 564/240

(58) Field of Classification Search ................. 564/240; 514/634
See application file for complete search history.

(56) References Cited

U.S. PATENT DOCUMENTS 5,830,917 A * 11/1998 Moore et al. ................. 514/634

OTHER PUBLICATIONS

Huang et al, J. Med. Chem., 2000, 43, 2938-2945.*
Huang et al, J. Med. Chem., 1999, 42, 3147-3153.*
Hah et al, J. Med. Chem., 2001, 44, 2667-2670.*

* cited by examiner

*Primary Examiner*—Shailendra Kumar
(74) *Attorney, Agent, or Firm*—Reinhart Boerner Van Deuren s.c.

(57) ABSTRACT

Peptidomimetic compositions for selective inhibition of neuronal nitric oxide synthase.

4 Claims, 19 Drawing Sheets

1, n = 1
2, n = 2
3, n = 3

4, n = 1
5, n = 2
6, n = 3

7, n = 1
8, n = 2
9, n = 3

Figure 5. A proposed model for binding of the *retro-inverso*-dipeptide amide 3 and 4 (prior art) at the active site of nNOS.

Figure 6. A proposed model for binding of the *retro-inverso*-dipeptide amide 2 at the active site of nNOS.

Figure 7. Phenyl reduced amide bond peptidomimetics nNOS and iNOS activities of the 4-amino proline coupled dipeptide derivatives.

Figure 22
| | IC50 | |
|---|---|---|
| | nNOS(μM) | eNOS(μM) |
| E1-ethyl-OH | 106 | 1386 |
| E2-ethyl-OH | 168 | 1662 |
| E1-propyl-OH | 255 | 1762 |
| E2-propyl-OH | 490 | 1076 |
E1/E2-propyl-OH
| | IC50 | |
|---|---|---|
| | nNOS(μM) | eNOS(μM) |
| E1-ethyl-NH₂ | 2.4 | 1141 |
| E2-ethyl-NH₂ | 9.4 | 1342 |
| E1-propyl-NH₂ | 23.5 | 1395 |
| E2-propyl-NH₂ | 6.8 | 1529 |
E1/E2-propyl-NH₂

SELECTIVE NEURONAL NITRIC OXIDE SYNTHASE INHIBITORS

The United States government has certain rights to this invention pursuant to Grant No. GM49725 from the National Institutes of Health to Northwestern University.

This application claims priority benefit from application Ser. No. 10/963,416, filed Oct. 12, 2004, now abandoned which was a continuation of application Ser. No. 10/178,625 (now U.S. Pat. No. 6,803,486) filed Jun. 24, 2002, which in turn claimed priority from provisional application Ser. No. 06/300,130 filed Jun. 22, 2001 and provisional application Ser. No. 60/315,587 filed Aug. 29, 2001, all of which are incorporated herein in their entirety.

BACKGROUND OF THE INVENTION

Nitric oxide (NO) is synthesized enzymatically from arginine in numerous tissues and cell types by a family of enzymes, collectively known as nitric oxide synthase (NOS, E.C. 1.14.13.39). Three principal isoforms of this enzyme have been isolated and characterized, each associated with different physiological functions: the immune response (inducible NOS or iNOS), smooth muscle relaxation (endothelial NOS or eNOS), and neuronal signaling (neuronal NOS or nNOS). All of these isoforms utilize NADPH, FAD, FMN, (6R)-5,6,7,8-tetrahydrobiopterin and heme as cofactors.

Overproduction of NO has been a factor in numerous disease states. NO overproduction by nNOS has been implicated in strokes, migraine headaches, Alzheimer's disease, and with tolerance to and dependence on morphine. iNOS-mediated overproduction of NO has been associated with development of colitis, tissue damage and inflammation, and rheumatoid arthritis.

Animal studies and early clinical trials suggest that NOS inhibitors could be therapeutic in many of these disorders; however, because of the importance of nitric oxide to physiological functioning, potent as well as isoform-selective inhibitors are essential. nNOS inhibition has been targeted for treatment of strokes, and iNOS inhibition for the treatment of septic shock and arthritis. Although there may be pathologies associated with overactivity of eNOS, blood pressure homeostasis is so critical that most investigators believe that therapeutically useful NOS inhibitors should not inhibit eNOS.

Excellent inhibitory potency and selectivity for nNOS over eNOS and iNOS have been achieved with certain prior art (FIG. 1) nitroarginine dipeptide amides that have an amine-containing side chain (1-3). See Huang, H.; Martasek, P.; Roman, L. J.; Masters, B. S. S.; Silverman, R. B. $N^{\omega}$-Nitroarginine-Containing Dipeptide Amides. Potent and Highly Selective Inhibitors of Neuronal Nitric Oxide Synthase. *J. Med. Chem.* 1999, 42, 3147-53.

The most potent nNOS inhibitor among these compounds is L-Arg$^{NO2}$-L-Dbu-NH$_2$ (1) (K$_i$=130 nM), which also shows excellent selectivity over eNOS (>1500-fold) and 192-fold selectivity over iNOS. Further, peptidomimetic modifications are, however, invariably necessary before such compounds can be therapeutically useful. Generally, peptides have poor bioavailability and are generally unsuccessful drug candidates.

The foregoing background information, together with other aspects of the prior art, is described more fully and better understood in light of the following publications: (1) Kerwin, J. F., Jr.; Lancaster, J. R., Jr. Nitric Oxide; A New Paradigm for Second Messengers. *Med. Res. Rev.* 1994, 14, 23-74; (2) Kerwin, J. F., Jr.; Heller, M. The Arginine-Nitric Oxide Pathway: A Target for New Drugs. *J. Med. Chem.* 1995, 38, 4342-62; (3) Stuehr, D. J.; Griffith, O. W. Mammalian Nitric Oxide Synthases. *Adv. Enzymol. Relat. Areas Mol. Biol.* 1992, 65, 287-346; (4) MacMicking, J.; Xie, Q. W.; Nathan, C. Nitric Oxide and Macrophage Function. *Annu. Rev. Immunol.* 1997, 15, 323-50; (5) Forstermann, U.; Pollock, J. S.; Schmidt, H. H. H. W.; Heller, M.; Murad, F. Calmodulin-Dependent Endothelium-Derived Relaxing Factor/Nitric Oxide Synthase Activity is Present in the Particulate and Cytosolic Fractions of Bovine Aortic Endothelial Cells. *Prot. Natl. Acad. Sci. U.S.A.* 1991, 88, 1788-92; (6) Schmidt, H. H. H. W.; Walter, U. NO at Work. *Cell* 1994, 78, 919-25; (7)(a) Choi, D. W.; Rothman, S. M. The role of glutamate neurotoxicity in hypoxic-ischemic neuronal death. *Annu. Rev. Neurosci.* 1990, 13, 171-82; (b) Garthwaite, J. *In the NMDA Receptor*; Watkins, J. C. Collingridge, G. L., Eds.; Oxford University Press.; Oxford, England, 1989; pp 187-205; (8) Thomson, L. L.; Iversen, H. K.; Lassen, L. H.; Olesen, J. The role of nitric oxide in the migrane pain. *CNS Drugs* 1994, 2, 417-22; (9) Dorheim, M. A.; Tracey, W. R.; Pollock, J. S.; Grammas, P. Nitric Oxide synthase activity is elevated in brain microvessels in Alzheimer's disease. *Biochem. Biophys. Res. Commun.* 1994, 205, 659-65; (10) Bhargava, H. N. Attenuation of tolerance to, and physical dependence on, morphine in the rat by inhibition of nitric oxide synthase. *Gen. Pharmacol.* 1995, 26, 1049-53; (11) Seo, H. G.; Takata, I.; Nakamura, M.; Tatsumi, H.; Suzuki, K.; Fujii, J.; Taniguchi, N. Introduction of nitric oxide and concommittant suppression of superoxide dismutase in experimental colitis in rats. *Arch. Biochem. Biophys.* 1995, 324, 41-7; (12) Kubes, P.; Suzuki, M.; Granger, D. N. Nitric Oxide; an endogeneous modulator of leukocyte adhesion. *Proc. Natl. Acad. Sci. U.S.A.* 1991, 88, 4651-5; (13) Maclintyre, I.; Zaidi, M.; Towhidul Alam, A. S. M.; Datta, H. K.; Moonga, B. S.; Lidbury, P. S.; Hecker, M.; Vane, J. R. Osteoclastic inhibition; an action of nitric oxide not mediated by cyclic GMP. *Proc. Natl. Acad. Sci. U.S.A.* 1991, 88, 2936-40; (14) Kilbourn, R. G.; Jubran, A.; Gross, S. S.; Griffith, O. W.; Levi, R.; Adams, J.; Lodato, R. F. Reversal of endotoxin-mediated shock by $N^G$-methyl-L-arginine, an inhibitor of nitric oxide synthesis. *Biochem. Biophys. Res. Commun.* 1990, 172, 1132-8; (15)(a) Collins, J. L.; Shearer, B. G.; Oplinger, J. A.; Lee, S.; Garvey, E. P.; Salter, M.; Duffy, C.; Burnette, T. C.; Furfine, E. S, N-Phenylamidines as selective inhibitors of human neuronal nitric oxide synthase. Structure-activity studies and demonstration of in vivo activity. *J. Med. Chem.* 1998, 41. 2858-71; (16) Wright, C. W.; Rees, D. D.; Moncada, S. Protective and Pathological roles of nitric oxide in endotoxin shock. *Cardiovasc. Res.* 1992, 26, 48-57; (17) Garvey, E. P.; Oplinger, J. A.; Furfine, E. S.; Kiff, R. J.; Laszlo, F.; Whittle, B. J. R.; Knowles, R. G. 1400W is a slow, tight binding, and highly selective inhibitor of inducible nitric oxide synthase in vitro and in vivo. *J. Biol. Chem.* 1997, 272, 4959-63; (18) Huang, H; Martasek, P.; Roman, L. J.; Masters, B. S. S.; Silverman, R. B. $N^{\omega}$-Nitroarginine-Containing Dipeptide Amides. Potent and Highly Selective Inhibitors of Neuronal Nitric Oxide Synthase. *J. Med. Chem.* 1999, 42, 3147-53.

DESCRIPTION OF THE DRAWINGS

FIGS. 18-22 show synthetic routes in preparation of several representative compounds of this invention and selective NOS activities available therewith.

SUMMARY OF THE INVENTION

Figure 1:
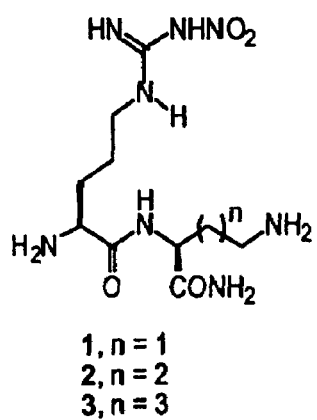
FIG. 1 shows several peptidomimetic compounds of the prior art.

In light of the foregoing, it is an object of the present invention to provide peptidomimetic compositions and/or related methods for their use in the inhibition of nitric oxide synthase, thereby addressing various issues and concerns of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide a bioisosteric model for the design of a wide variety of nitric oxide synthase inhibitors.

It is an object of the present invention to provide peptidomimetic, argininyl and/or guanidinyl compositions, which can be used selectively or otherwise in the inhibition of one or more NOS isoforms.

It can also be an object of the present invention, alone or in conjunction with any other objective, to provide an NOS inhibitor composition incorporating one or more amine nitrogen centers, which can be utilized in conjunction with enzyme active site interaction.

It can also be an object of the present invention, alone or in conjunction with any other objective, to provide an NOS inhibitor composition with a reduced amide bond, as can be utilized to enhance the stability of such compositions towards in vivo endogenous peptidases.

It can also be an object of the present invention to provide compositions, such as those described herein, designed with a degree of conformational control so as to maintain and/or enhance desired selective inhibition.

It can also be an object of the present invention to provide a method of using dipeptide and analogous structures of the type illustrated herein to determine spatial orientation with respect to an NOS isoform and correlate observed activity/selectivity to such structure or orientation.

It can also be an object of the present invention, more specifically, to provide such dipeptides and/or structurally-related analogues, including proline moieties and the use thereof to affect NOS activity.

It can also be an object of the present invention to provide a method of using proline substitution and associated stereo- and regiochemistry to affect dipeptide structure, conformation and resulting enzymatic interaction.

Other objects, features, benefits and advantages of the present invention will be apparent from this summary and its descriptions of various preferred embodiments, and will be readily apparent to those skilled in the art having knowledge of nitric oxide synthase inhibition. Such objects, features, benefits and advantages will be apparent from the above as taken in conjunction with the accompanying examples, data, figures and all reasonable inferences to be drawn therefrom.

In part, the present invention includes an N-nitroarginine-containing dipeptide composition as can be represented by a structural formula of the type provided in claim 1, below, as described elsewhere herein and/or consistent with structures provided in one or more of the accompanying figures. Without limitation, $R_1$ can include but is not limited to hydrogen, alkyl, and a prolinyl (2-carboxypyrrolidinyl and/or a, below) moiety. Such alkyl and/or prolinyl moieties can include one or more substituents of the type described herein or as could be contemplated by those skilled in the art made aware of this invention, such substitutes as can reflect reagents used and/or choice or design of synthetic pathway. $R_2$ can include but is not limited to amino, alkyl, aminoalkyl, aminoprolinamide (or 2-carbamoylpyrrolidinyl and/or b, c and d below) moiety and a diaminocyclopentanecarboxamide (or diaminoacetamidocyclopentanyl moiety and/or e and f, below) moiety. Likewise, such $R_2$ moieties can be substituted as referenced above, described herein or as would otherwise be known to those skilled in the art made aware of this invention, such substituents including but not limited to hydroxy and azido groups.

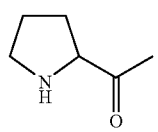

(a)

-continued

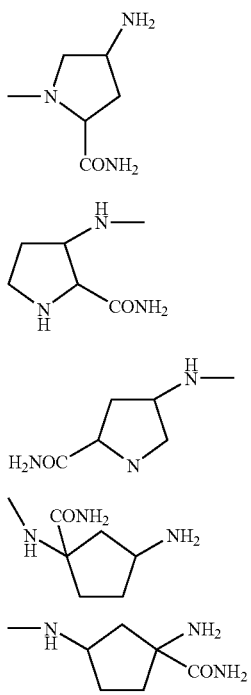

As described elsewhere herein, these and other compositions of the present invention can be provided, depending upon synthetic method, choice of reagents and/or end use application as, without limitation, one of any number of salts, hydrates, solvates, stereoisomers, diastereomers and/or mixtures thereof. In particular, such a composition can be a hydrate, a salt and/or a mixture of stereoisomers. In various preferred compositions, $R_1$ is either hydrogen or a 4-aminoprolinyl moiety.

In part, the present invention can also include a dipeptide composition having an N-nitroarginine residue coupled with an amide bond, at a terminus of the nitroarginine residue, to an amino-substituted proline residue. Such a composition, as would be represented in the art, has a formula of either $Arg^{NO2}\text{-}Pro^{NH2}$, where the substituted proline residue is coupled to the N-terminus of the nitroarginine residue, or $Pro^{NH2}\text{-}Arg^{NO2}\text{-}NH_2$, where the substituted proline residue is coupled to the C-terminus of the nitroarginine residue. In preferred embodiments, the proline residue is coupled to the N-terminus of the nitroarginine residue, the latter of which has a stereochemical configuration corresponding to the D-isomer, the L-isomer or a mixture thereof. Highly preferred embodiments of such compositions, as supported by their inhibition activities, have a nitroarginine residue with an L-configuration, and a proline residue with a 4-amino substituent and a trans-diastereomeric configuration.

Accordingly, the present invention further includes a method of using a proline residue to affect nitric oxide synthase inhibition. Such a method includes (1) providing a dipeptide composition having an N-nitroarginine residue coupled with an amide bond, at a terminus of the nitroarginine residue, to an amino-substituted proline residue, such a dipeptide composition as described above or represented by one or more of the structural formula provided herein; and (2) interacting the dipeptide composition with an isoform of nitric oxide synthase, such composition in an amount and/or interaction at a time sufficient, under effective conditions, to inhibit nitric oxide synthase activity on an available arginine substrate. In preferred embodiments of such a method, the dipeptide composition can be one of the dipeptides described above. In highly preferred embodiments, the proline residue has a 4-amino substituent, is coupled to the C-terminus of the nitroarginine residue, and has a trans-diastereomeric configuration. Such a composition, among others described herein, can selectively inhibit the neuronal isoform of nitric oxide synthase, over the inducible and endothelial isoforms thereof.

In part, the present invention can also include a peptidomimetic N-nitroguanidinyl composition as can be represented by the structural formula.

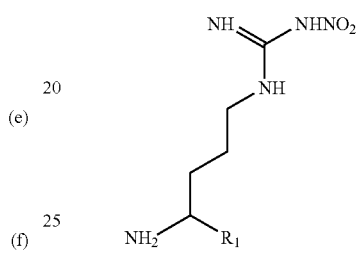

Therein, $R_1$ is $XNHR_2$, where X is a moiety selected from the group consisting of $CH_2$ and $C(O)$. $R_2$ can include but is not limited to a variety of moieties of the type described herein. For instance, in various preferred embodiments, $R_2$ can be an alkylamine, wherein the alkyl portion thereof can be methyl, ethyl or propyl, but also can include higher homologs and/or their isomers as would be understood by those skilled in the art. In various other embodiments, $R_2$ can be alkylpyridinyl, with the alkyl portion thereof positioned ortho, meta or para with respect to the heterocyclic nitrogen center. In preferred such embodiments, the alkyl portion can vary, but is preferably of 1 or 2-carbon length. Alternatively, the pyridine ring system ($R_2$) can be bonded directly to the nitrogen center of $R_1$. In various other embodiments, $R_2$ can be an alkylphenylalkylamine moiety, where the alkyl portions can vary in carbon length and with position relative one to another on the phenyl ring. Representative, non-limiting structures of such $R_2$ moieties are as provided, below. As shown and discussed elsewhere, moities such as $R_2$ can, in the broader context of this invention, be substituted (e.g., hydroxy, amino, alkyl, etc.) as would be understood by those skilled in the art made aware of this invention, depending on reagent choice and synthetic method using straightforward modifications of the techniques described herein.

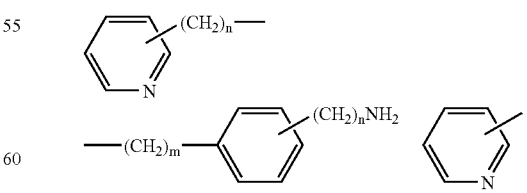

Regardless, in preferred peptidomimetic compositions, X is a $CH_2$ moiety and/or $R_2$ is an alkylamine. Alternatively, where X is a $CH_2$ moiety, $R_2$ can be one of various other $R_2$ selections, provided above or as described elsewhere herein.

Figure 4:
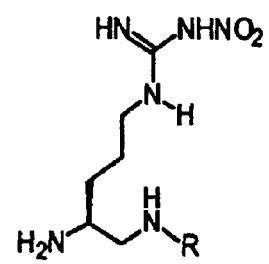
FIG. 4 provides a generic structural formula of a class of compositions included in this invention, in accordance with various reduced-amide compounds described elsewhere herein, such a formula relating, but not limited, to the compounds of FIG. 3 and other compounds provided in subsequent figures, charts and/or tables.

Alternatively, various preferred embodiments of the present invention include one of numerous peptidomimetic N-nitroguanidinyl compositions having the formula shown in FIG. 4. In particular, R can be an alkyl or aromatic/heterocyclic amine. Preferably, but without limitation, R is an alkylamine, alkylphenylamine, alkylpyridine, or phenylalkylamine substituent, the alkyl moiety of which is methylene, $(CH_2)_n$, or a homolog thereof with n=1-3 (alkylamine), n=0-2 (alkylphenylamine), n=0-2 (alkylpyridine), or n=0-2 (phenylalkylamine). Other compositional embodiments are discussed below, in the context of various conformational considerations. Such compositions include, without limitation, any salts, hydrates, solvates, prodrugs, metabolites, stereoisomers, diastereomers, isosteres and/or mixtures thereof.

In part, the present invention is also directed to one or more methods for the selective inhibition of the neuronal isoform of nitric oxide synthase-catalyzed production of nitric oxide. Such a method includes the interaction or binding of one of the present compositions, preferably an N-nitroguanidinyl composition, with an isoform of nitric oxide synthase, particularly neuronal synthase. Compositions useful in conjunction with the present method include those described more fully above, such compositions as can be formulated and/or utilized in amounts sufficient to inhibit nitric oxide formation via the corresponding isoform, preferably with selective inhibition of the neuronal isoform over the inducible and endothelial isoforms. More particularly, such compositions are utilized in amounts sufficient to affect synthase activity on arginine substrates. The composition interaction and isoform inhibition can be determined or analyzed by arginine conversion, or the decrease thereof, and measured by various spectroscopic and/or assay techniques.

More specifically, the present invention also includes a method of using reduced amide argininyl compositions to inhibit isoforms of nitric oxide synthase. Such compositions include those discussed more fully, above. The interaction or binding thereof with an isoform of nitric oxide synthase, in the presence of one or more co-factors of the sort described herein, serve to inhibit production of nitric oxide. As with other methods of this invention, effective levels or quantities of such compounds will be readily determined by those skilled in the art made aware of this invention, as will techniques and procedures for their use.

In part, consistent with the preceding and as additional embodiments one or more of the compositional variations provided herein, this invention can also be directed to a peptidomimetic compound of a formula provided in claim 1. In such compositions, R can be selected from $CH_2CH(OH)(CH_2)_nX$ moieties, where n is an integer selected from one, two and about three, terminating with either a hydroxy or an amino group X. In certain embodiments, the alkyl component of such a moiety can be ethyl or propyl. Regardless, and without limitation, various enantiomers are available using synthetic techniques of the sort described below. Likewise, depending upon synthetic method, choice of reagents and/or application, such compounds can further include any one of a number of salts, hydrates, solvates, stereoisomers, diastereomers and/or mixtures thereof. In particular, such a compound can be a hydrate, a salt and/or a mixture of enantiomers designated as E1 and/or E2, in one or more, of the accompanying figures.

In part, this invention can also be directed to a method of using an N-nitroguanidinyl compound to correlate nitric oxide synthase inhibition with the structure of such a compound. Such a method comprises the interaction, binding and/or contact of such a compound with an isoform of nitric oxide synthase in an amount sufficient to inhibit nitric oxide formation and/or correlate the structure of the compound with such inhibitory activity. Compositions useful in conjunction with such methods include those described more fully above, using the techniques described herein or as would otherwise be known to those skilled in the art and made aware of this invention.

DETAILED DESCRIPTION OF CERTAIN EMBODIMENTS

Figure 2:
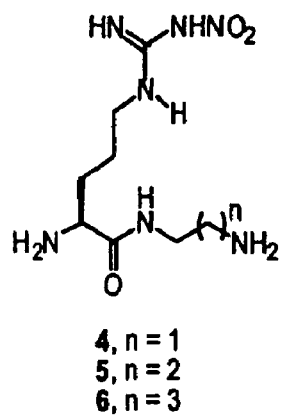
FIG. 2 shows several of a class of compositions of the present invention, descarboxamide derivatives of the corresponding prior art compounds of FIG. 1. Other such derivatives are also contemplated in conjunction herewith.

Illustrating the design and development of several preferred embodiments of this invention, peptidomimetic modifications were made on prior art compounds 1-3. (FIG. 1) Huang, H; Martasek, P.; Roman, L. J.; Silverman, R. B. Synthesis and Evaluation of Peptidomimetics as Selective Inhibitors and Active Site Probes of Nitric Oxide Synthase. *J. Med. Chem.* 2000, 43, 2938-45. Incorporation of protecting groups at the N-terminus of the dipeptide and masking of the NH— group of the peptide bond resulted in a dramatic loss in potency of nNOS, demonstrating importance of the α-amino group of the dipeptide and NH-moiety of the peptide bond for binding at the enzyme active site. Removal of the carboxamide group (compositions 4-6, FIG. 2), as one modification associated with this invention, had an effect (see Table 1) on both potency and selectivity.

Of the many possible bioisosteric modifications of the amino or NH moieties, the reduced amide bond (—$CH_2$—NH—) was considered. Representative compounds 7-9 (FIG. 3) contain features beneficial to inhibition of NOS: First, several amine nitrogen centers, useful for interaction with the enzyme active site; and second, a lack of amide bonding for in vivo stability toward endogenous peptidases.

Figure 3:
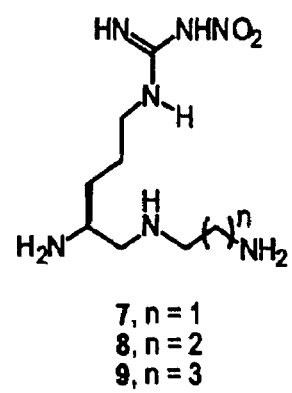
FIG. 3 shows, in accordance with this invention, several of another class of preferred compounds, also useful for NOS inhibition.

With reference to FIG. 3 and examples 1-8, reduced amide bond analogues (7-9) were synthesized according to the methods of Scheme 1, using Weinreb amide 10 as an intermediate. Nahm, S.; Weinreb, S. M. N-Methoxy-N-methylamides as effective acylating agents. *Tetrahedron Lett.* 1981, 22, 3815-8. The Weinreb amide was reduced to an aldehyde using lithium aluminum hydride according to a modified procedure of Goel et al. Goel, O. P.; Krolls, U.; Stier, M.; Kesten, S. N-tert-Butoxycarbonyl-L-Leucinal. Organic Syntheses 1988, 67, 68-71. The resulting N-Boc-nitro-L-argininal (11) and mono Boc-protected alkanediamines (12) were reductively coupled using sodium triacetoxyborohydride in dry methanol, providing the reduced dipeptides 13. Tamura, S. Y.; Semple, J. E.; Ardecky, R. J. Novel and General Method for the Preparation of Peptidyl Arginals. *Tetrahedron Lett.* 1996, 37, 4109-12. Graham, S. L.; deSolms, S. J.; Guiliani, E. A.; Kohl, N. E.; Mosser, S. D.; Oliff, A. L.; Pompliano, D. L.; Rands, E.; Breslin, M. H.; Deana, A. A.; Garsky, V. M.; Scholz, T. H.; Gibbs, J. B.; Smith, R. L. Pseudpeptide Inhibitors of Ras Farnesyl-Protein Transferase. *J. Med. Chem.* 1994, 37, 725-32. After purification of these compounds, cleavage of the Boc groups was achieved with TFA. Compositions 7-9 were isolated as pale yellow powders after lyophilization, and the elemental analyses showed that all of these compounds were triple trifluoroacetic acid dihydrate salts. As described elsewhere herein, analogous procedures can be used to prepare various other reduced amide bond compositions.

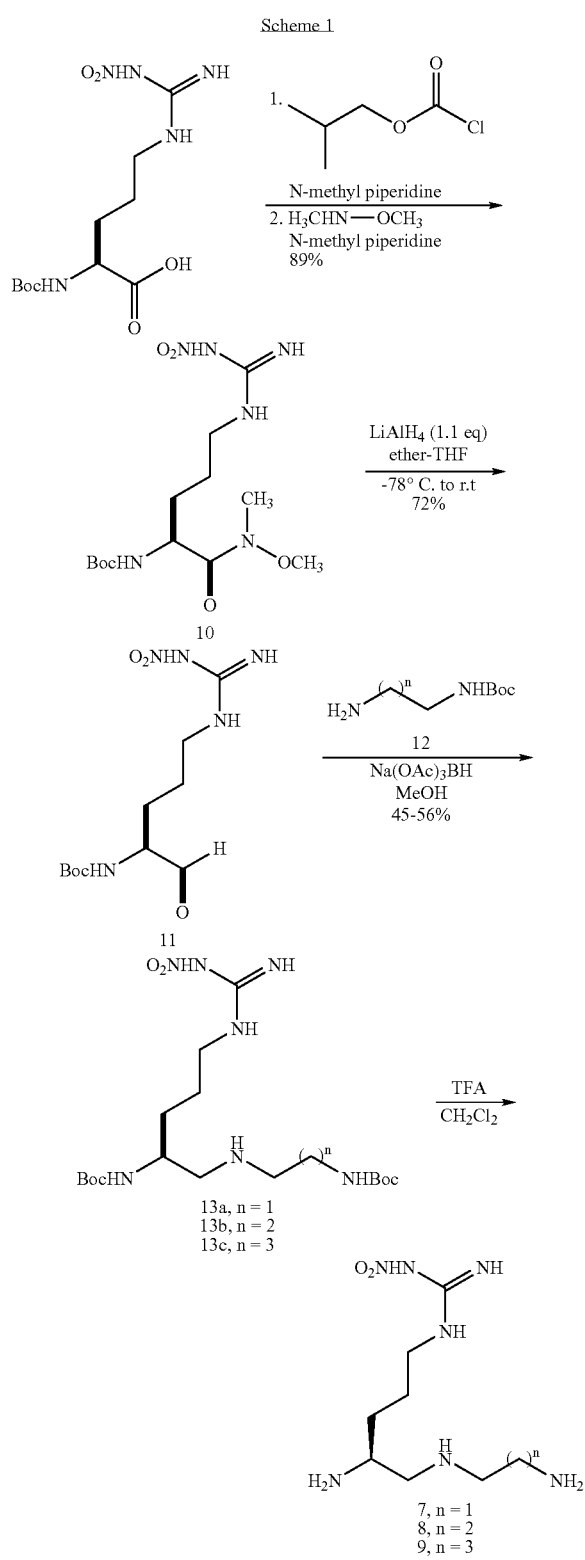

Scheme 1

The $K_i$ data for the reduced amide bond analogues (7-9) are given in Table 1, below, along with the data for the corresponding dipeptides (1-3) and descarboxamide analogues (4-6). Reduction of the carbonyl group of the amide bond either preserves or improves the potency toward nNOS. Compound 7 shows the best potency over nNOS ($K_i$=120 nM) as well as the highest selectivity over eNOS (>2500-fold) and iNOS (320-fold) in these series of compounds. The length of the amine side chain seems to have only a minor effect on the potency for all isoforms of NOS; 8 and 9 inhibit nNOS with $K_i$ values of 290 nM and 460 nM, respectively. However, the shorter chain has better potency as well as selectivity.

TABLE 1

NOS Inhibition by the Reduced-Amide Bond Analogues 7-9 and $N^\omega$-Nitroarginine-Containing Dipeptides (1-6)[a]

| | $K_i$ (μM)[b] | | | Selectivity[c] | |
|---|---|---|---|---|---|
| | NNOS | INOS | ENOS | eNOS/nNOS | iNOS/nNOS |
| 1[d] | 0.13 | 25 | 200 | 1538 | 192 |
| 2[d] | 0.33 | 97 | 245 | 742 | 294 |
| 3[d] | 0.45 | 104 | 141 | 313 | 231 |
| 4[e] | 0.54 | 100 | 199 | 368 | 185 |
| 5[e] | 0.46 | 118 | 213 | 463 | 256 |
| 6[e] | 0.35 | 108 | 70 | 200 | 308 |
| 7 | 0.12 | 39 | 314 | 2617 | 325 |
| 8 | 0.29 | 73 | 524 | 1807 | 252 |
| 9 | 0.46 | 123 | 411 | 893 | 267 |

With reference to Table 1, [a]the enzymes used for the $K_i$ measurements are recombinant rat nNOS, recombinant murine iNOS, and recombinant bovine eNOS. [b] The $K_i$ values represent at least duplicate measurements; standard deviations of ±8-12% were observed. [c] The ratio of $K_i$ (eNOS or iNOS) to $K_i$(nNOS); all are nNOS-selective. [d] Data taken from Huang, H; Martasek, P.; Roman, L. J.; Masters, B. S. S.; Silverman, R. B. N $N^\omega$-Nitroarginine-Containing Dipeptide Amides. Potent and Highly Selective Inhibitors of Neuronal Nitric Oxide Synthase. *J. Med. Chem.* 1999, 42, 3147-53. [e] Data taken from Huang, H; Martasek, P.; Roman, L. J.; Silverman, R. B. Synthesis and Evaluation of Peptidomimetics as Selective Inhibitors and Active Site Probes of Nitric Oxide Synthase. *J. Med. Chem.* 2000, 43, 2938-45.

Comparing the data for compositions 7-9 with those for 4-6, to examine the intrinsic effect of deletion of the amide carbonyl group, the potency on nNOS and iNOS are about the same or increased, but the potency with eNOS has greatly decreased. In particular, the large increase in selectivity for nNOS over eNOS by 7 appears related to a 4.5-fold increase in potency for nNOS and a 1.5-fold decrease in potency for eNOS. For 8 and 9 this selectivity increase is believed driven more by large decreases in potency for eNOS (2.5-fold and almost 6-fold, respectively). The selectivity for nNOS over eNOS is significantly increased for 7-9, perhaps with the implication that the carbonyl moiety of the amide bond might not be necessary for its activity toward nNOS and iNOS, but that the rigid —CO—NH— group interacts better with the active site of eNOS than the reduced, flexible —CH₂—NH— group. The difference may also be the result of the nonbasic amide nitrogen becoming basic when reduced to the corresponding amine, which may not bind as well to eNOS. Regardless, the data demonstrates that reduced amide bond peptidomimetics of this invention, as illustrated by compositions 7-9, are significant surrogates for the dipeptide inhibitors of nNOS.

Libraries of nitroarginine-containing dipeptides, dipeptide esters, and dipeptide amides have been synthesized as possible candidates for nNOS-inhibition based on two observations. First, the prior art L-nitroarginine (L-NA) itself is a potent and selective nNOS-inhibitor ($K_i$=15 nM for nNOS, and 39 nM for eNOS) and has about 250-fold selectivity in favor of nNOS over iNOS. Second, as mentioned above, L-arginine-containing dipeptides (e.g., L-Arg$^{NO2}$-L-Dbu-NH$_2$) are good substrates for the various isoforms of NOS, suggesting that the active site of NOS is flexible enough to accommodate larger molecules than arginine. Indeed, crystal structures of the oxygenase domains of eNOS and iNOS show there is a large opening, which allows the diffusion of both the substrate and the product (L-arginine and L-citrulline). Furthermore, there are significant structural differences between isoforms just outside of the substrate-binding pocket. From these two aspects, it was hypothesized that dipeptides containing nitroarginine could fit into the active site of NOS, and at the same time utilize the structural differences to achieve isoform selectivity.

Twelve nitroarginine (L-, or D-) containing dipeptides and dipeptide esters were synthesized in the standard way, and 152 dipeptide amides were prepared using a solid-phase synthesis method, and they were tested against each isoform of NOS. Among these libraries of compounds, several dipeptides were found to be potent and nNOS-selective inhibitors. The dipeptide amides containing amino acids with a nitrogen-containing side chain, such as Lys, Orn, Dbu, were relatively potent inhibitors of nNOS. They also have great selectivity over eNOS implying that the terminal amine group is significant for the selectivity over eNOS. Among the dipeptide esters, D-Phe-D-Arg$^{NO2}$-OMe showed excellent selectivity for nNOS over iNOS (1800-fold), although the potency is weak and the selectivity for nNOS over eNOS is minimal. See U.S. Pat. No. 6,274,557, the entirety of which is incorporated herein by reference.

Figure 5:
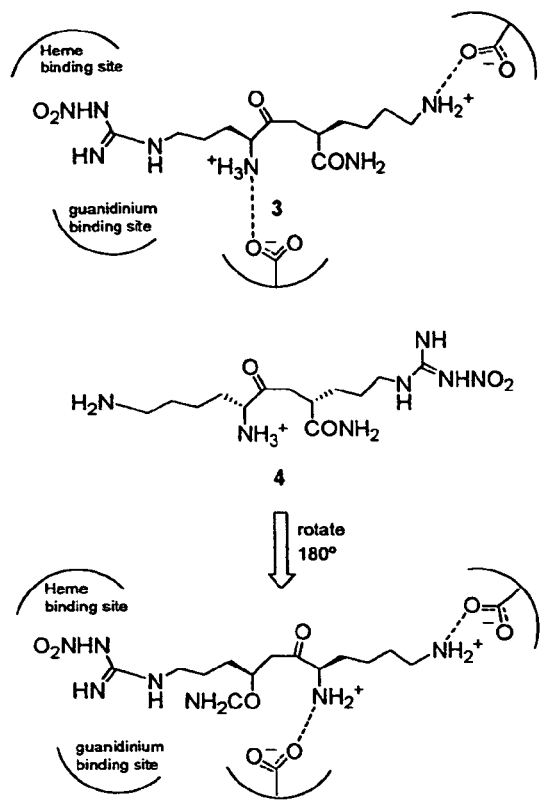
FIG. 5 provides in schematic format a proposed model for binding of the retro-inverso-dipeptide amides 3 and 4 (prior art) at the active site of nNOS such model as can be used as described herein.

Without limitation, when L-Arg$^{NO2}$ is at the N-terminus of the dipeptide inhibitors, it appears an L-amino acid is also favored at the C-terminus. But when Arg$^{NO2}$ is at the C-terminus, the amino acid was more selective as the D-isomer. From these observations, a retro-inverso-dipeptide model was proposed. In this case, the nitroarginine residue binds to the same binding site, regardless of its position in the dipeptide (FIG. 5). For example, D-Arg$^{NO2}$ of (schematic 4 in FIG. 5), may flip over 180° to assume an L-Arg$^{NO2}$ configuration (like schematic 3 in FIG. 5) at the N-terminus for binding (FIG. 5). Molecular modeling and energy minimization of the retro-inverso-dipeptide amides (schematics 3 and 4 in FIG. 5) gave perfect overlap; furthermore, recent ENDOR spectroscopic results confirmed that the dipeptides bind to holo-nNOS similarly from the point of view of the nitroguanidino functionality.

Figure 6:
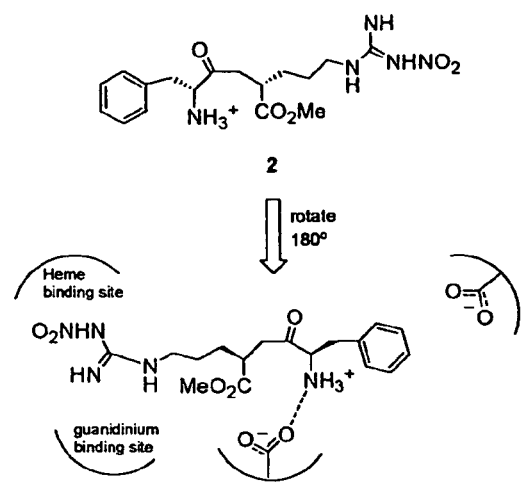
FIG. 6, in schematic format, provides another proposed model for binding of the retro-inverso-dipeptide amide 2 at the active site of nNOS.

If a retro-inverso binding model holds for prior art D-Phe-D-Arg$^{NO2}$-OMe (2) at the active site of nNOS, then it can be expected to bind as shown in FIG. 6. An important terminal nitrogen interaction of schematic 1 (or schematic 3, 4 in FIG. 5) in the active site is lost; instead the phenyl ring moiety replaces the C-terminal residue active site: explaining the weaker potency and minimal selectivity for nNOS over eNOS of 2 (FIG. 6). However, the replacement of the phenyl ring could also attribute to the high selectivity of nNOS over iNOS (1800-fold); it would not be expected as effective as the amine group moiety at the nNOS active site, but much more unfavorable in the active site of iNOS.

Figure 7:
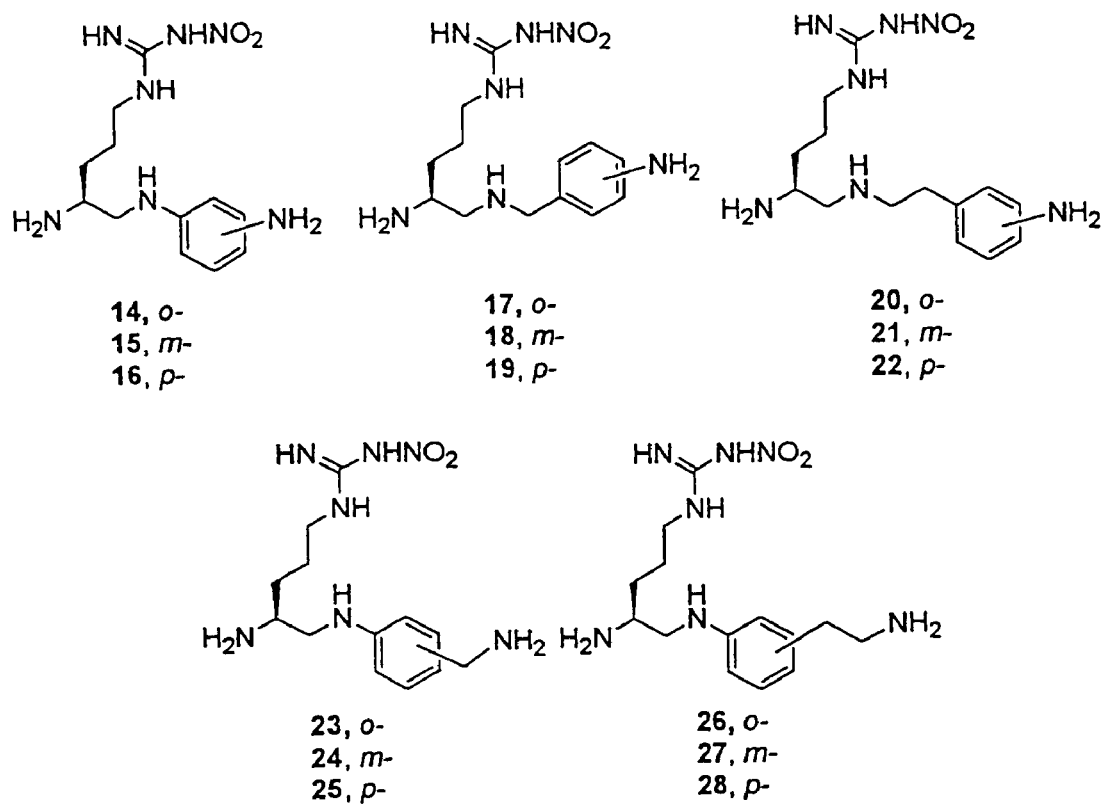
FIG. 7 shows, without limitation, various substituted phenyl, reduced amide bond peptidomimetic compositions, in accordance with this invention.
Figure 8:
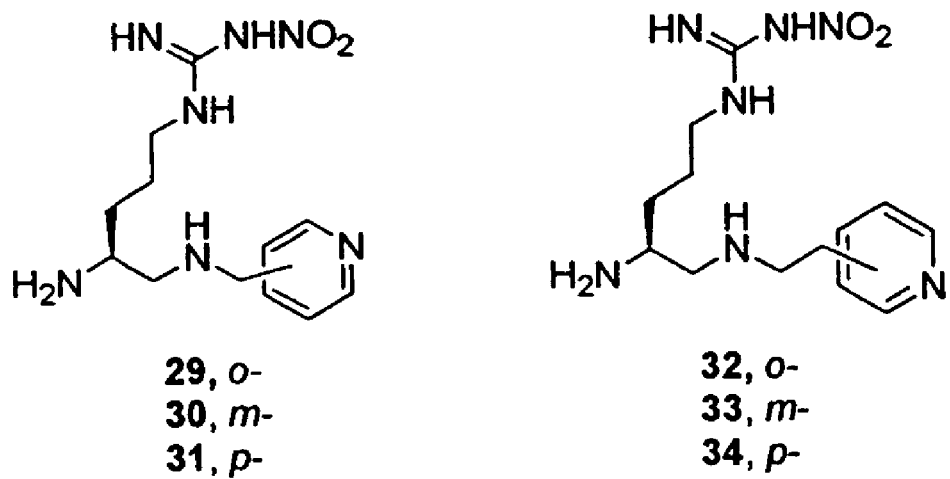
FIG. 8 shows, without limitation, a number of representative pyridinyl, reduced amide bond peptidomimetic compositions, also in accordance with this invention.

Without limitation to any one theory or mode of operation, the present invention can be considered in light of the foregoing hypothesis: selectivity for nNOS over eNOS derived from the terminal nitrogen, with selectivity over iNOS from an aromatic ring moiety. Accordingly, the present invention can provide a basis for design of numerous compositions: such as but not limited to nNOS-selective inhibitors having an aromatic ring and terminal nitrogen moieties within a dipeptide-like structure. As discussed above, it was also contemplated that a successful surrogate of the amide bond, namely, the reduced-amide bond, could be incorporated into such a structure. Based on such considerations and observations, the present invention further includes various heterocyclic or aromatic, reduced-amide bond peptidomimetic compounds as selective inhibitors of nNOS. (See FIGS. 7 and 8, with reference to FIGS. 3 and 4.)

TABLE 2

NOS Inhibition by the aromatic, reduced-amide analogs.[a]

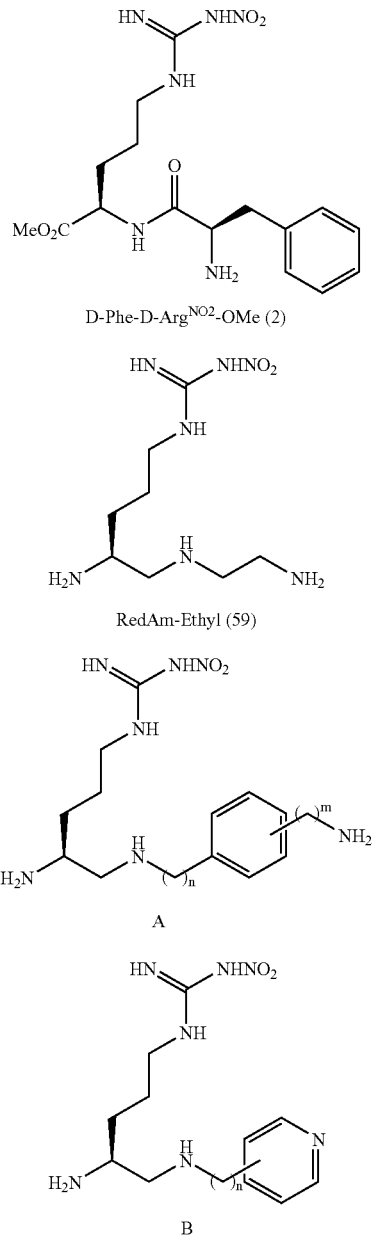

| Compound | K$_i$ (μM)[b] | | | Selectivity[c] | |
|---|---|---|---|---|---|
| | nNOS | iNOS | eNOS | iNOS/nNOS | ENOS/nNOS |
| D-Phe-D-Arg$^{NO2}$-OMe (2)[d] | 2 | 3600 | 5 | 1800 | 2.5 |
| RedAm-Ethyl (59) | 0.12 | 39 | 314 | 320 | 2577 |
| 15 (A, n = 0, m = 0, m-) | 2.20 | 279 | 78.6 | 127 | 36 |

TABLE 2-continued

NOS Inhibition by the aromatic, reduced-amide analogs.[a]

| | | | | | |
|---|---|---|---|---|---|
| 16 (A, n = 0, m = 0, p-) | 2.28 | 339 | 116 | 149 | 51 |
| 17 (A, n = 1, m = 0, o-) | 20.3 | 86.3 | 86.1 | 4.25 | 4.24 |
| 18 (A, n = 1, m = 0, m-) | 2.06 | 572 | 185 | 278 | 90 |
| 19 (A, n = 1, m = 0, p-) | 1.60 | 326 | 303 | 204 | 189 |
| 20 (A, n = 2, m = 0, o-) | 1.36 | 184 | 30.1 | 135 | 22.1 |
| 21 (A, n = 2, m = 0, m-) | 1.36 | 166 | 47.6 | 122 | 35 |
| 22 (A, n = 2, m = 0, p-) | 0.74 | 339 | 170 | 458 | 230 |
| 23 (A, n = 0, m = 1, o-) | 5.55 | 29.3 | 39.8 | 5.28 | 7.17 |
| 24 (A, n = 0, m = 1, m-) | 0.21 | 80 | 194 | 381 | 924 |
| 25 (A, n = 0, m = 1, p-) | 1.37 | 335 | 409 | 245 | 299 |
| 26 (A, n = 0, m = 2, o-) | 0.05 | 3.51 | 105 | 70.2 | 2121 |
| 27 (A, n = 0, m = 2, m-) | 2.21 | 260 | 100 | 118 | 45.2 |
| 28 (A, n = 0, m = 2, p-) | 1.66 | 360 | 414 | 217 | 249 |
| 29 (B, n = 1, o-) | 2.90 | 154 | 443 | 53 | 1153 |
| 30 (B, n = 1, m-) | 0.55 | 141 | 523 | 256 | 951 |
| 31 (B, n = 1, p-) | 1.59 | 392 | 589 | 247 | 370 |
| 32 (B, n = 2, o-) | 2.21 | 72.6 | 123 | 33 | 254 |
| 33 (B, n = 2, m-) | 2.06 | 178 | 275 | 86 | 133 |
| 34 (B, n = 2, p-) | 0.76 | 395 | 193 | 520 | 56 |

With reference to Table 2, [a]the $K_i$ values are calculated from the measured $IC_{50}$ values and the enzymes used are recombinant rat nNOS, recombinant murine iNOS, and recombinant bovine eNOS. [b]The $K_i$ values represent at least duplicate measurements; standard deviations of ±8-12% were observed. [c]The ratio of $K_i$(eNOS or iNOS) to $K_i$ (nNOS); all are nNOS selective. [d]Data taken from ref 10.

With reference to examples 10-38, below, compounds (14-34) were prepared by reductive amination, using N-Boc-L-nitroargininal (35) as the key intermediate and it was coupled with various aromatic diamines.

Compounds 17-22 were synthesized according to Scheme 2. N-Boc-L-nitroargininal (26) was coupled with (2-, 3-, 4-aminomethyl)anilines (36-38), and [2-,3-,4-(2-aminoethyl)]anilines (39-41), respectively. The reductive amination was performed in decent yield without protection of the aniline group because alkyl amines are much more reactive than aniline.

Scheme 2.
Synthesis of the benzyl, reduced-amide bond analogs (17-22).

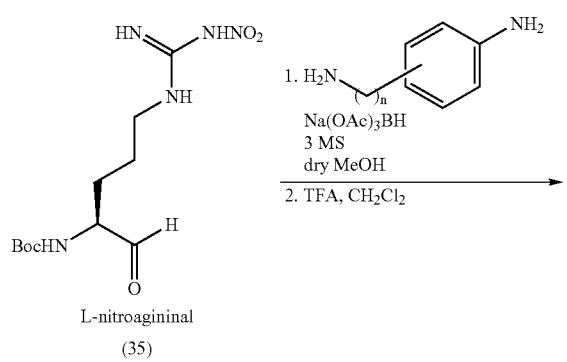

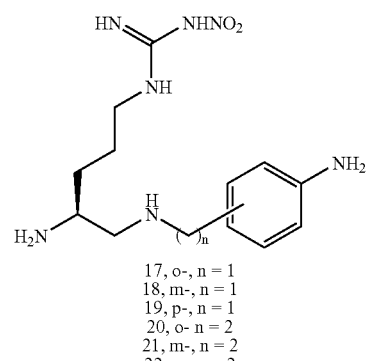

17, o-, n = 1
18, m-, n = 1
19, p-, n = 1
20, o-, n = 2
21, m-, n = 2
22, p-, n = 2

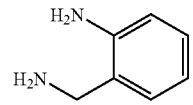

36

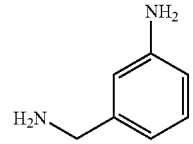

37

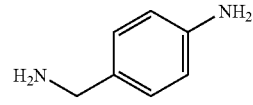

38

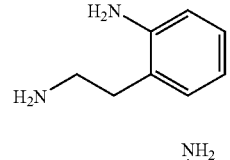

39

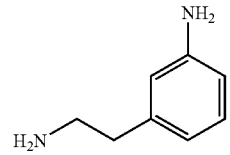

40

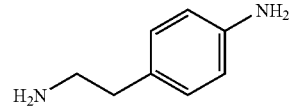

41

Most of the corresponding aromatic diamines were commercially available, but 2- and 3-(2-aminoethyl)aniline (39, 40) were synthesized (Scheme 3). The closest starting materials were the corresponding (nitrophenyl)acetonitriles, which were sequentially reduced by $BH_3$-THF complex and tin chloride-hydrate to give 39 and 40.

Scheme 3. Synthesis of 39 and 40

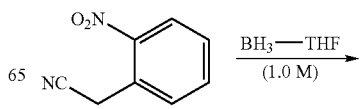

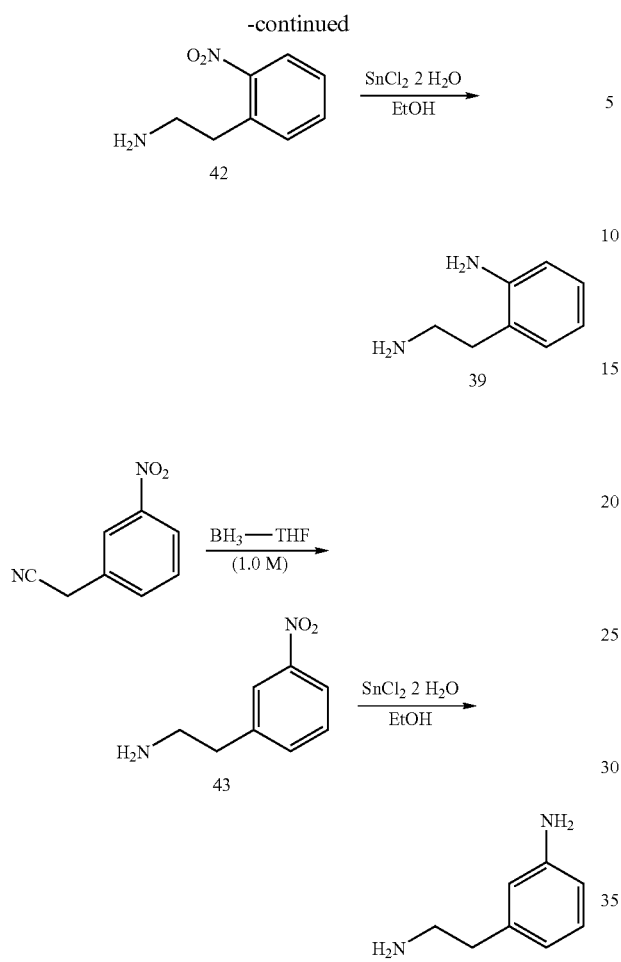

The aniline amino group of the same (aminoalkyl)anilines (36-41) also were coupled with N-Boc-L-nitroargininal (Scheme 4). In this case, protection of the alkylamine moieties preceded the reductive amination (except 45 and 48 were commercially available). Using two equivalents of (aminoalkyl)aniline was enough for mono protection, while eight equivalents was necessary for the monoprotection of α,ω-dialkylamine in the reference.

Scheme 4.
Synthesis of the benzyl, reduced-amide bond analogs (15-16, and 23-28).

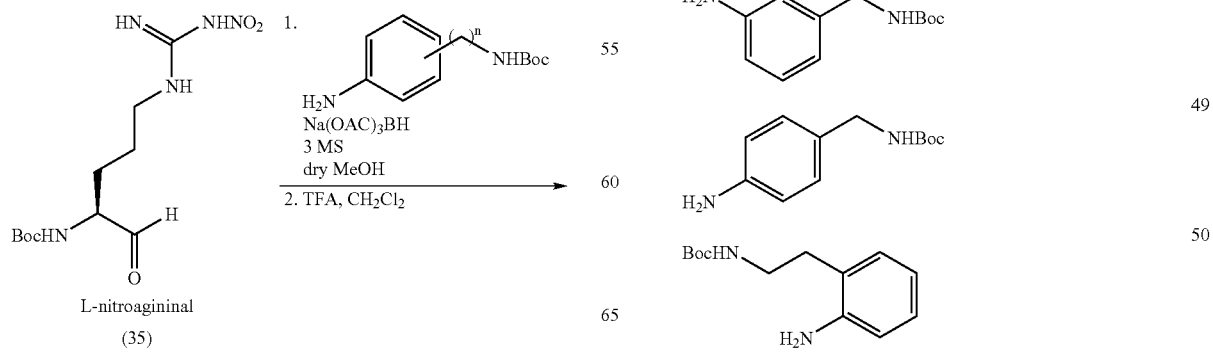

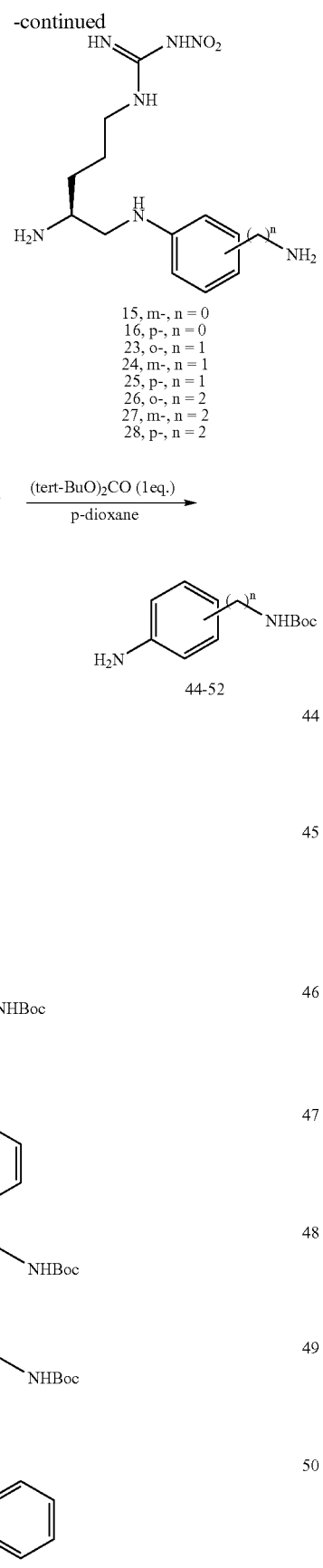

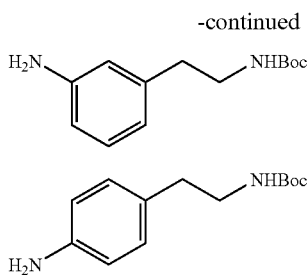

51

52

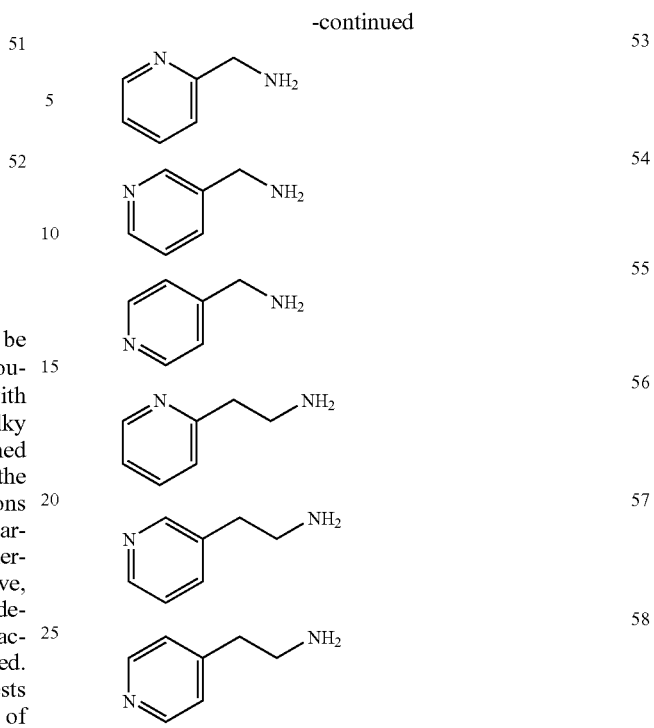

53

54

55

56

57

58

Among these target molecules, 14 (FIG. 7) could not be made using the same synthetic method. The reductive coupling of mono-Boc-protected benzene-1,2-diamine (44) with N-Boc-L-nitroargininal was not successful, and the bulky Boc-group was thought to be the reason. However it turned out that the low reactivity of benzene-1,2-diamine, not the steric factor, was the cause, because the reductive aminations with either free benzene-1,2-diamine or mono-methylcarbamated benzene-1,2-diamine proved to be fruitless. Furthermore, N-Boc-L-nitroargininal is also somewhat unreactive, since it exists as two forms; cyclized hemiaminal and aldehyde in solution. To accomplish this reaction, different reaction conditions; other than reductive amination are needed. But further investigation was postponed until enzyme tests show that the series is potent enough to warrant synthesis of this analogue.

Scheme 5 shows the synthetic route for the pyridyl, reduced-amide bond analogs. All of the aminoalkyl pyridines (53-58) were commercially available, and in each case the reductive amination with N-Boc-L-nitroargininal worked well.

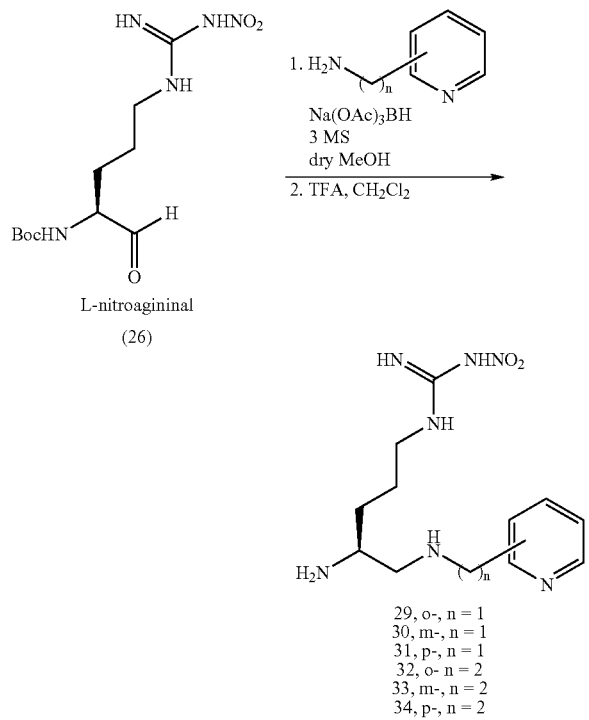

Scheme 5.
Synthesis of the pyridyl, reduced-amide bond analogs (29-34).

29, o-, n = 1
30, m-, n = 1
31, p-, n = 1
32, o- n = 2
33, m-, n = 2
34, p-, n = 2

Figure 9:
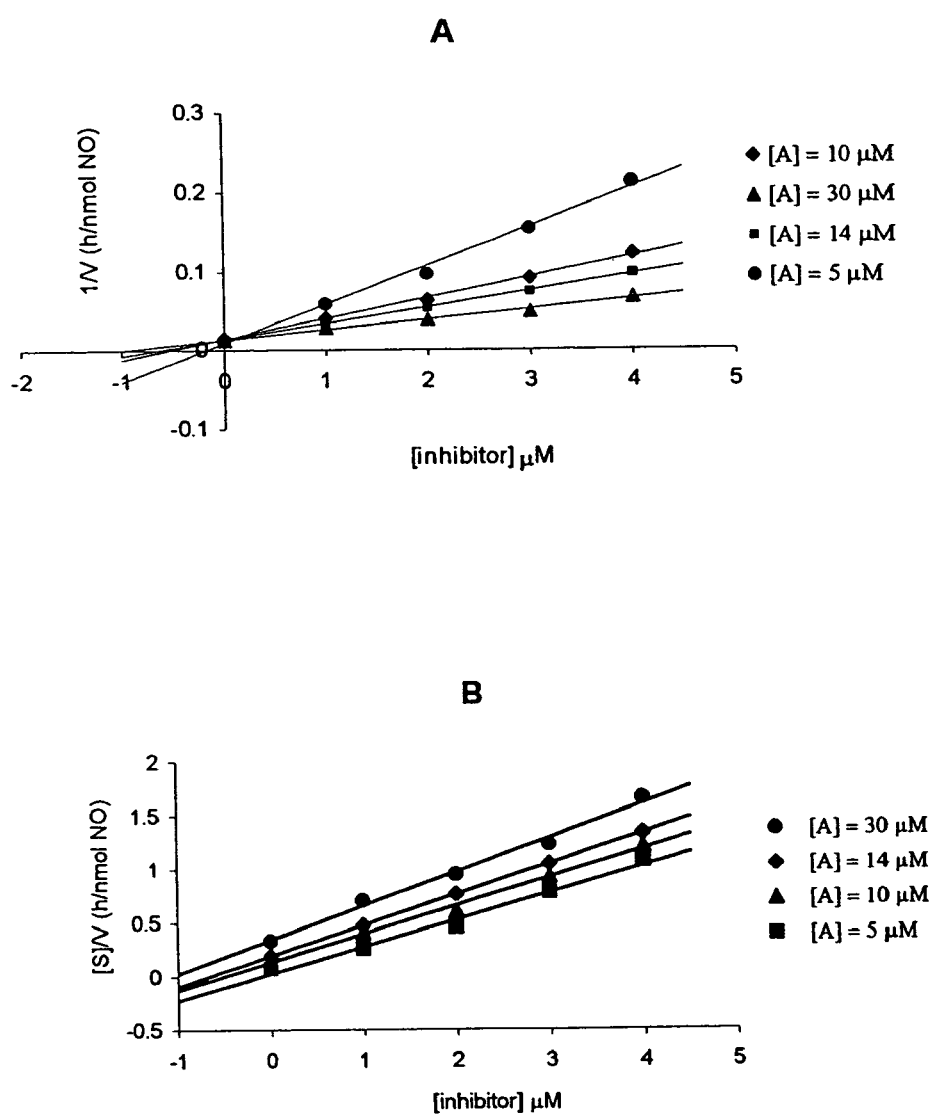
FIG. 9 shows several inhibition patterns, consistent with results available through use of the present invention; A: Dixon plot of competitive inhibition of nNOS by composition 26; and B: Cornish-Bowden plot of competitive inhibition.
Figure 10:
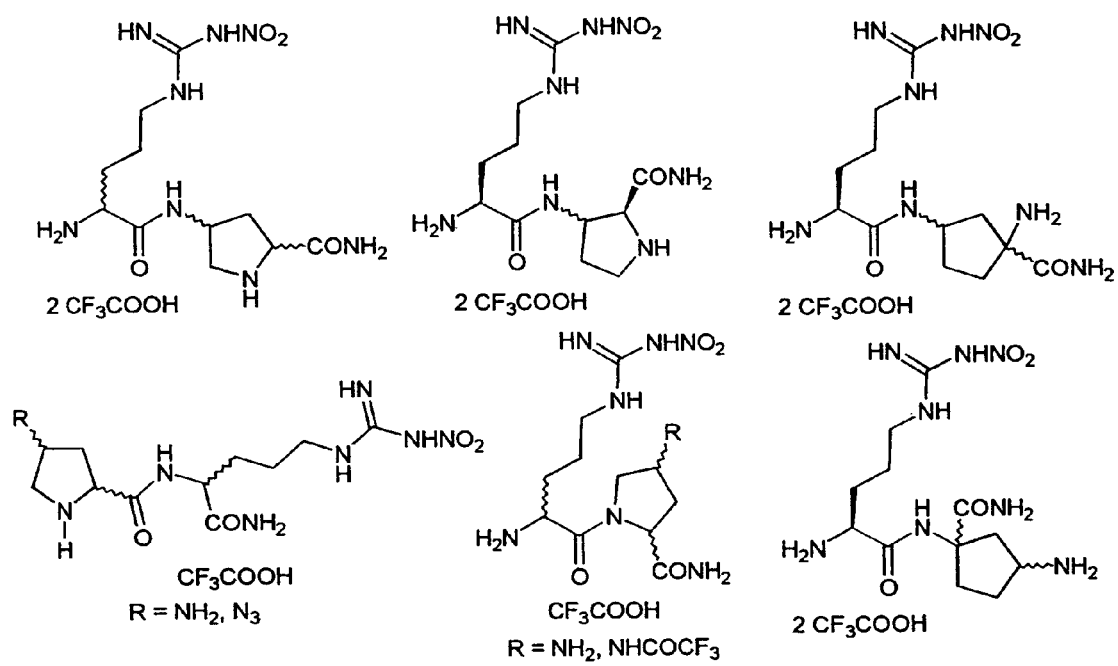
FIG. 10 shows, without limitation, various argininyl and/or peptidomimetic compositions, substituted in accordance with this invention for conformational restriction and/or control. Consistent with broader aspects of this invention, several structures provided therein reflect, without limitation, several of numerous representative substituents and possible isomeric and/or diastereomeric configurations.

All products from the coupling reactions were purified by column chromatography using various solvent systems, and the Boc group was deprotected in 30% TFA/methylene chloride. They showed >90% purity by HPLC. All twenty compounds were tested on each isozyme of NOS to determine $IC_{50}$ values. All of the aromatic, reduced-amide analogues are competitive inhibitors of the three isoforms of NOS. Representative plots for the competitive inhibition of nNOS by 26 are shown in FIG. 9. Dixon analysis and the method of Cornish and Bowden were used to determine the type of inhibition. The $K_i$ data for the aromatic, reduced-amide bond analogues (15-34) are given in Table 2 along with the data for the prior art D-Phe-D-Arg$^{NO2}$-OMe and the reduced-amide ethyl (RedAm-ethyl) analog (59).

As shown in the Table 2, all tested aromatic, reduced-amide bond analogues as representative of this invention, were found to be nNOS-selective inhibitors. When compared to the non-aromatic compound, RedAm-ethyl (59), the potencies on nNOS are decreased (except 26), but most of compounds showed still higher potency than the prior art D-Phe-D-Arg$^{NO2}$-OMe. The potencies with iNOS were also decreased from those of 59 except for 23 and 26, but not as low as the aforementioned prior art compound. However, the $K_i$ value with iNOS is closer to that of 59 or prior art L-Arg$^{NO2}$-L-Dbu-NH$_2$ rather than to D-Phe-D-Arg$^{NO2}$-OMe, indicating that a desired unfavorable interaction of the aromatic moiety in the iNOS active site did not occur in this series.

The first two benzenediamine compounds (15, 16) were found to be less satisfactory inhibitors of nNOS and iNOS than the RedAm-ethyl (59), while having little difference toward eNOS inhibition. This results in the dramatic decrease of isoform selectivity of nNOS over eNOS (from 2577-fold to 36 and 51-fold). This implies the amino residue of the C-terminal phenyl ring is not long enough for an effective interaction with the tetrahydrobiopterin. Further, these two compounds would not be preferred drug candidates because they were found to be unstable in the Hepes buffer (pH 7.5), the medium for the enzyme assay.

The (aminomethy)laniline series (17-19) are also less preferred as inhibitors of nNOS and iNOS. The rigid C-terminal aniline structure does not seem to be favored for the interaction with $H_4B$ in the nNOS active site. This is clear in the case of the o-isomers (17, 23), which showed almost the same potency with all of the isozymes, thereby resulting in the loss of isoform selectivity. However, when the (aminomethyl) aniline moiety was attached at the anilineamino group (but the same length, 23-25), a much better result was obtained for the m-isomer (24), indicating that a flexible amino residue is better for selective interaction with nNOS; also, spatial geometry appears to be a consideration. Compound 24 showed almost the same potency and selectivity as RedAm-ethyl (59) implying that the spatial geometry in the enzyme active site is similar.

The inhibitory potency of the (aminoethyl)aniline series 20-22 and 26-28 also varied depending on the location of the rigid phenyl ring. It appears that the p-isomer is preferred when in phenyl ring is at the C-terminus (22), but the o-isomer is much more preferred when the flexible alkylamine residue is at the C-terminus (26) in this length of compounds. Compound 26 was the best nNOS inhibitor ($K_i$=0.05 µM) of all of the compounds this series, and the isoform selectivity over eNOS was also excellent (>2000-fold); however the selectivity over iNOS is only 70-fold.

The variation of the inhibitory potencies with nNOS as a result of a small structural change was also found in the pyridinyl series (29-34). While they are generally weak inhibitors of nNOS; 30 was the best of these compounds, with good isoform selectivity over iNOS and eNOS. While the predicted increase in isoform selectivity of nNOS over iNOS was not fully realized in the aromatic, reduced-amide bond peptidomimetic compositions, a high potency with nNOS as well as high selectivity of nNOS over eNOS as retained in some of these compounds (24, 26, 30), as well as good selectivity over iNOS.

Yet another consideration germane to this invention is steric and/or conformational control of the inhibitor compositions. With reference to the prior art, the dipeptide L-Arg$^{NO2}$-L-Dbu-NH$_2$, the L-Dbu fragment has free rotation with respect to the aminoethyl side chain. Determination of the exact spatial position of the amino group at the enzyme is difficult, and also there might be a loss of activity and/or selectivity because of conformational flexibility. Accordingly, L-Arg$^{NO2}$-L-Dbu-NH$_2$ can also be used as a point for development of conformationally restricted dipeptide derivatives and/or related peptidomimetic compositions having a degree of conformational control, in accordance with this invention.

Accordingly, in part, the present invention includes numerous dipeptide compositions, including but not limited to those shown in FIGS. 10-17. Such compositions include, without limitation, any possible salts, hydrates, solvates, prodrugs, metabolites, stereoisomers, diastereomers, isosteres and/or mixtures thereof, as would be understood by those skilled in the art.

More specifically, the present invention also includes a method of using proline substitution of a dipeptide structure to affect and/or inhibit nitric oxide synthase activity. Such proline-substituted compositions include those discussed more fully herein. The interaction or binding thereof with an isoform of nitric oxide synthase, optionally in the presence of one or more co-factors of the sort described herein, serve to inhibit production of nitric oxide. As with other methods of this invention, effective levels or quantities of such compositions will be readily determined by those skilled in the art made aware of this invention as will various techniques and procedures for their use.

In accordance therewith, dipeptides and/or peptidomimetic compositions of this invention have also been synthesized using an exocyclic nitrogen on a proline derivative to form the dipeptide bond. Such structures provide rigid analogs of the aforementioned prior art compounds but without a substituted peptide bond. Some of these compositions were the most potent of any described herein (see, FIG. 17).

Trans derivatives were more potent than cis derivatives in these series. 4N-(L-Arg$^{NO2}$)-L-trans-Pro$^{4NH2}$-NH$_2$ 71 is the most potent compound with an IC$_{50}$ of 0.5 µM. This compound represents the first conformationally restricted analog of L-Arg$^{NO2}$-L-Dbu-NH$_2$, with a similar IC$_{50}$ and selectivity over iNOS. L-Arg$^{NO2}$-containing dipeptides were more potent than D-Arg$^{NO2}$ analogs. The diastereomer, 4N-(L-Arg$^{NO2}$)-D-trans-Pro$^{4NH2}$-NH$_2$, 100 showed a greater selectivity over iNOS. D-Arg$^{NO2}$-containing dipeptides showed IC$_{50}$ higher than 100 µM. Intriguingly, L-trans-4-aminoproline-containing dipeptides are the most potent compounds in all the series (see compounds 69 and 87 in Tables 3 and 4, in conjunction with several examples, below.). This indicates which conformation of L-Arg$^{NO2}$-L-Dbu-NH$_2$ interacts with the enzyme.

Trans derivatives were purified by HPLC affording 210 mg of the most potent compound 4N-(L-Arg$^{NO2}$)-L-trans-Pro$^{4NH2}$-NH$_2$ b 71, 10 mg of 4N-(D-Arg$^{NO2}$)-L-trans-Pro$^{4NH2}$-NH$_2$ 99, 30 mg of 4N-(D-Arg$^{NO2}$)-D-trans-Pro$^{4NH2}$-NH$_2$ 101, and 180 mg of 4N-(L-Arg$^{NO2}$)-D-trans-Pro$^{4NH2}$-NH$_2$ 100. Compound 74 has been assayed against nNOS (IC$_{50}$=0.73 µM) and iNOS (IC$_{50}$=13.5 µM). This compound is less selective than 71 against iNOS but their potencies against nNOS are similar. The cis isomer of compound 74 showed an IC$_{50}$=100 µM against nNOS and an IC$_{50}$ higher than 100 µM against iNOS. This result clearly stresses the importance of the irans configuration on the conformationally restricted analogs of L-Arg$^{NO2}$-L-Dbu-NH$_2$. For instance, the diastereomer mixture of the compound 78 showed an IC$_{50}$ against nNOS higher than 100 µM.

The present invention also provides a pharmaceutical composition comprising a dipeptide or peptidomimetic composition of this invention in conjunction with a physiologically or otherwise suitable formulation. In a preferred embodiment, the present invention includes one or more NOS inhibitors as set forth above formulated into compositions together with one or more non-toxic physiologically tolerable or acceptable diluents, carriers, adjuvants or vehicles that are collectively referred to herein as diluents, for parenteral injection, for oral administration in solid or liquid form, for rectal or topical administration, or the like. The resulting compositions can be, in conjunction with the various methods described herein, administered to humans and animals either orally, rectally, parenterally, intracistemally, intravaginally, intraperitoneally, locally, or as a buccal or nasal spray.

Compositions suitable for parenteral administration can comprise physiologically acceptable sterile aqueous or non-aqueous solutions, dispersions, suspensions or emulsions and sterile powders for reconstitution into such sterile solutions or dispersions. Examples of suitable diluents include water, ethanol, polyols, suitable mixtures thereof, vegetable oils and injectable organic esters such as ethyl oleate. Proper fluidity can be maintained, for example, by the sue of a coating such a lecithin, by the maintenance of the required particle size in the case of dispersions and by the use of surfactants.

Compositions can also contain adjuvants such as preserving, wetting, emulsifying, and dispensing agents. Prevention of the action of microorganisms can be insured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form can be brought about by the use of agents delaying absorption, for example, aluminum monostearate and gelatin. Besides such inert diluents, the composition can also include sweetening, flavoring and perfuming agents. Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonit, agar—agar and tragacanth, or mixtures of these substances, and the like.

EXAMPLES OF THE INVENTION

The following non-limiting examples and data illustrate various aspects and features relating to the compositions and/or related methods of the present invention, including the use of reductive amination and/or the resulting guanidinyl compositions, the aforementioned descarboxamide compositions, and those prepared to afford or examine conformational control—all as are available through the synthetic methodologies described herein. In comparison with the prior art, the present compositions and related methods provide results and data which are surprising, unexpected, and contrary to the prior art. While the utility of this invention is illustrated through the use of several compositions and methods which can be used therewith, it will be understood by those skilled in the art that comparable results are obtainable with various other compositions and/or their methods of use, as are commensurate with the scope of this invention.

General Methods. NOS assays were recorded on a Perkin-Elmer Lambda 10 UV/vis spectrophotometer. $^1$H NMR spectra were recorded on a Varian Inova 500-MHz NMR spectrometer. Chemical shifts are reported as δ values in parts per million downfield from TMS (δ 0.00) as the internal standard in $CDCl_3$. For samples run in $D_2O$, the HOD resonance was arbitrarily set at 4.80 ppm. An Orion Research model 701 pH meter with a general combination electrode was used for pH measurements. Electrospray mass spectra were obtained on a Micromass Quattro II spectrometer. Elemental analyses were obtained by Oneida Research Services, Inc., Whiteboro, N.Y. Thin-layer chromatography was carried out on E. Merck precoated silica gel 60 $F_{254}$ plates. Amino acids were visualized with a ninhydrin spray reagent or a UV/vis lamp. E. Merck silica gel 60 (230-400 mesh) was used for flash column chromatography.

High-performance liquid chromatography was performed on a Beckman System Gold (Model 125P solvent module and Model 166 detector). In case of analytical HPLC, samples were analyzed by elution from a Hypersil ODS $C_{18}$ column (Agilent, 5 μm, 4.0×250 mm), with a flow rate of 1 μL/min. The mobile phase was a gradient from 100% solvent A (0.1% TFA in water) and 0% solvent B (0.1% of TFA in $CH_3CN$) to 60% solvent A and 40% solvent B over 5 min, then to 30% solvent A and 70% solvent B over 20 min and to 100% solvent A over 10 min. Sample elution was detected by absorbance at 254 nm. For the purification of final products, a Whatman Partsil $C_{18}$ semi-prep HPLC column (9.4×125 mm) was used. Samples were eluted using a gradient of 100% solvent A (0.1% TFA in water) to 70% of solvent B (0.1% of TFA in $CH_3CN$) over 30 min at a flow rate of 4 mL/min.

Reagents and Materials. Amino acids were purchased from Advanced ChemTech, Inc. NADPH, calmodulin, and human ferrous hemoglobin were obtained from Sigma Chemical Co. Tetrahydrobiopterin ($H_4B$) was purchased from Alexis Biochemicals. HEPES, DTT and conventional organic solvents were purchased from Fisher Scientific. 2,3,4-(aminomethyl) aniline was purchased from TCI, America. All other chemicals were purchased from Aldrich, unless otherwise stated.

Enzyme and Assay. All of the NOS isoforms used were recombinant enzymes overexpressed in E. coli from different sources; there is very high sequence identity for the isoforms from different sources. The murine macrophage iNOS was expressed and isolated according to the procedure of Hevel et al. Hevel, J. M.; White, K. A.; Marletta, M. A Purification of the Inducible Murine Macrophage Nitric Oxide Synthase. *J. Biol. Chem.* 1991, 266, 22789-91. The rat nNOS was expressed (Roman, L. J.; Sheta, E. A.; Martasek, P.; Gross, S. S.; Liu, Q.; Masters, B. S. S. High Level Expression of Functional Rat Neuronal Nitric Oxide Synthase in *Escherichia coli*. *Proc. Natl. Acad. Sci. U.S.A.* 1995, 92, 8428-32) and purified as described. Martasek, P.; Liu, Q.; Roman, L. J; Gross, S. S.; Sessa, W. C.; Masters. B. S. S. Characterization of Bovine Endothelial Nitric Oxide Synthase Expressed in *Escherichia coli*. *Biochem, Biophys. Res. Commun.* 1996, 219, 359-65. The bovine eNOS was isolated as reported. Martasek. P.; Liu, Q.; Roman, L. J.; Gross, S. S.; Sessa, W. C.; Masters B. S. S. Characterization of Bovine Endothelial Nitric Oxide Synthase Expressed in *Escherichia coli*. *Biochem. Biophys. Res. Commun.* 1996, 219, 359-65. Nitric oxide formation from NOS was monitored by the hemoglobin capture assay as described. Hevel, J. M.; Marletta, M. A Nitric Oxide Synthase Assays. *Methods Enzymol.* 1994, 133, 250-8.

With respect to examples 4-8, a typical assay mixture for nNOS contained 10 μM arginine, 1.6 mM $CaCl_2$, 11.6 μg/ml calmodulin, 100 μM dithiotheitol, 100 μM NADPH, 6.5 μM tetrahydrobiopterin, and 3 mM oxyhemoglobin in 100 mM Hepes buffer (pH 7.5). The mixture for the iNOS assay included 10 μM arginine, 100 μM dithiotheitol, 100 μM NADPH, 6.5 μM tetrahydrobiopterin, and 3 mM oxyhemoglobin in 100 mM Hepes buffer (pH 7.5). The assay mixture for eNOS contained 80 μM oxyhemoglobin, 10 μM arginine, 100 μM dithiotheitol, 10 μM $CaCl_2$, 1 μg/ml calmodulin, 5 μM tetrahydrobiopterin, and 100 μM NADPH in 50 mM Hepes buffer (pH 7.5). All assays were in a final volume of 600 μL and were initiated with enzyme. Nitric oxide reacts with oxyHb to yield methemoglobin which was detected at 401 nm ($\epsilon$=19700 $M^{-1}$ $cm^{-1}$) on a Perkin-Elmer Lambda 10 UV/vis spectrophotometer.

With, respect to examples 10-38, a typical assay mixture for nNOS contained 3-15 μM L-arginine, 1.6 mM $CaCl_2$, 11.6 μg/mL calmodulin, 100 μM DTT, 100 μM NADPH, 6.5 μM $BH_4$, and 3 mM oxyhemoglobin in 100 mM Hepes (pH 7.5). The reaction mixture for the iNOS assay included 10 μM L-arginine, 100 μM DTT, 100 μM NADPH, 6.5 μM $BH_4$, and 3 mM oxyhemoglobin in 100 mM Hepes (pH 7.5). The eNOS assay mixture contained 3-25 μM L-arginine, 10 μM $CaCl_2$, 1 μg/mL calmodulin, 100 μM DTT, 100 μM NADPH, 5 μM $BH_4$, and 80 μM oxyhemoglobin in 50 mM Hepes (pH 7.5). All assays were in a final volume of 600 μL and were initiated by enzyme. Nitric oxide reacts with oxyHb to yield methemoglobin which was detected at 401 nm ($\epsilon$=19700 $M^{-1}$ $cm^{-1}$) on a Perkin-Elmer Lambda 10 UV/vis spectrophotometer.

Inhibition Methods. The reversible inhibition of NOS was studied under initial rate conditions with the hemoglobin assay as described above. The apparent $K_i$ values were obtained by measuring percent inhibition in the presence of 10 μM L-arginine with at least three concentrations of inhibitor. The parameters of the following inhibition equation were fitted to the initial velocity data: % Inhibition=100-[I]/{[I]+

Example 1

N$^\alpha$-(tert-Butoxycarbonyl)-L-nitroarginine N-methyl-O-methylcarboxamide (10). This compound was prepared from 12.8 g (40.1 mmol) of N$^\alpha$-(tert-butoxycarbonyl)-L-nitroarginine as described in the reference below, except that isobutyl chloroformate was used instead of methyl chloroformate. The residue was further evacuated on an oil pump to give a white solid product (12.9 g, 89%): $^1$H NMR δ5.65 (d, 1H, N—H, J=9.0), 4.69 (t, 1H, J=9.0), 3.79 and 3.73 (s, 3H), 3.25 and 3.10 (s, 3H), 3.64 (m, 1H), 3.32 (m, 1H), 1.79 (m, 2H), 1.63 (m, 2H), 1.47 (s, 9H). Goel, O. P.; Krolls, U.; Stier, M.; Kesten, S, N-tert-Butoxycarbonyl-L-leucinal. *Org. Synth.* 1988, 67, 68-71.

Example 2

N$^\alpha$-(tert-Butoxycarbonyl)-L-nitroargininal (11). This compound was prepared according to the method in the reference below. From 3.62 g of 10 (10 mmol), the white powder product 2.17 g (72%) was obtained, and it was stored in a deep freezer (−80° C.) prior to use. $^1$H NMR showed that 11 is a mixture of the free aldehyde and cyclized hemiaminal. Tamura, S. Y.; Semple, J. E.; Ardecky, R. J. Novel and General Method for the Preparation of Peptidyl Arginals. *Tetrahedron Lett.* 1996, 37, 4109-12.

Example 3

(4S)-4-N-tert-Butoxycarbonylamino-5-(2-[N-tert-butoxycarbonyl aminoethyl]aminopentyl]-N'-nitroguanidine (13a). To a solution of 11 (303 mg, 1 mmol) in dry methanol, N$^\alpha$-tert-butoxycarbonyl-1,2-ethanediamine (12, n=1; 184 μl, 1 mmol) and 3 Å molecular sieves were added and stirred at room temperature. After being stirred for 1 h, the reaction mixture was treated with sodium triacetoxyborohydride (334.6 mg, 1.5 mmol) and stirred overnight. The reaction mixture was filtered, and the filtrate was concentrated in vacuo. The residue was purified by flash column chromatography on silica gel (EtOAc: MeOH=1:1) to afford 13a (201 mg, 45%) as a pale yellow solid: $^1$H NMR (500 MHz, CD$_3$OD) δ3.67 (m, 1H), 3.33 (m, 2H), 3.04-3.20 (m, 2H), 2.62-2.73 (m, 4H), 1.52-1.75 (m, 4H), 1.45 (brs, 18H).

Example 4

(4S)-4-N-tert-Butoxycarbonylamino-5-(2-[N-tert-butoxycarbonyl aminopropyl]aminopentyl]-N'-nitroguanidine (13b). This compound (234 mg, 51%) was prepared as described above using N$^\alpha$-tert-butoxycarbonyl-1,3-propanediamine (12b, n=2): $^1$H NMR (500 MHz, CDCl$_3$) δ4.90 (m, 1H), 3.69 (m, 1H), 3.18-3.21 (m, 4H), 2.77 (m, 2H), 2.64 (m, 2H), 1.50-1.65 (m, 6H), 1.44 (brs, 18H).

Example 5

(4S)-4-N-tert-Butoxycarbonylamino-5-(2-[N-tert-butoxycarbonyl aminobutyl]aminopentyl]-N'-nitroguanidine (13c). This compound (265 mg, 56%) was prepared as described above using N$^\alpha$-tert-butoxycarbonyl-1,4-butanediamine: $^1$H NMR (500 MHz, CDCl$_3$) δ4.67 (m, 1H), 3.71 (m, 1H), 3.14 (m, 4H), 2.72 (t, 2H, J=6.0), 2.64 (m, 2H), 1.71 (m, 2H), 1.49-1.54 (m, 8H), 1.45 (brs, 18H).

Example 6

(4S)-N-(4-Amino-5-[aminoethyl]aminopentyl)-N'-nitroguanidine (7). Compound 13a (201 mg, 0.45 mmol) was treated with 10 mL of trifluoroacetic acid/CH$_2$Cl$_2$ (1:1 v/v) for 30 min. Excess TFA and solvent were removed by evaporation. The residue was dissolved in a small amount of water, which was washed with ether and lyophilized to give a pale yellow foam (110 mg, 99%): $^1$H NMR (500 MHz, D$_2$O) δ3.63 (m, 1H), 3.32-3.39 (m, 6H), 3.24 (m, 2H), 1.69-1.78 (m, 4H). HRMS (M+1) calcd for C$_8$H$_{21}$N$_7$O$_2$ 248.183, found 248.180. Anal (C$_8$H$_{21}$N$_7$O$_2$.3TFA.2H$_2$O)C, H, N.

Example 7

(4S)-N-(4-Amino-5-[aminopropyl]aminopentyl)-N'-nitroguanidine (8). This compound was prepared as described above using compound 13b: $^1$H NMR (500 MHz, D$_2$O) δ3.62 (m, 1H), 3.32 (m, 2H), 3.24 (m, 2H), 3.13 (m, 2H), 3.01 (m, 2H), 2.03 (quin, 2H, J=7.0), 1.69-1.78 (m, 4H). HRMS (M+1) calcd for C$_9$H$_{23}$N$_7$O$_2$ 262.199, found 262.195. Anal (C$_9$H$_{23}$N$_7$O$_2$.3TFA.2H$_2$O)C, H, N.

Example 8

(4S)-N-(4-Amino-5-[aminobutyl]aminopentyl)-N'-nitroguanidine (9). This compound was prepared as described above using compound 13c: $^1$H NMR (500 MHz, D$_2$O) δ3.75 (m, 1H), 3.62 (m, 2H), 3.32 (m, 2H), 3.24 (m, 2H), 2.94 (m, 2H), 1.67-1.82 (m, 8H). HRMS (M+1) calcd for C$_{10}$H$_{25}$N$_7$O$_2$: 276.214, found 276.214. Anal (C$_{10}$H$_{25}$N$_7$O$_2$.3TFA2H$_2$O)C, H, N.

Example 9

Determination of K$_i$ Values. The apparent K$_i$ values were obtained by measuring percent inhibition in the presence of 10 μL-arginine with at least three concentrations of inhibitor. The parameters of the following inhibition equation (Segel, I. H. Enzyme Kinetics; John Wiley and Sons; New York, 1975; p105) were fitted to the initial velocity data: % inhibition=100 [I]/{[I]+K$_i$(1+[S]/K$_m$)}. K$_m$ values for L-arginine were 1.3 μM (nNOS), 8.2 μM (iNOS), and 1.7 μM (eNOS). The selectivity of an inhibitor was defined as the ratio of the respective K$_i$ values.

Example 10

General procedure for the Reductive amination of 15-34. To a solution of N$^\square$-(tert-butoxycarbonyl)-L-nitroargininal (1 equiv.) in dry methanol, aromatic diamine (1.5 equiv.) and 3 Å molecular sieves were added and stirred at the room temperature. After being stirred for 1 h, the reaction mixture was treated with sodium triacetoxyborohydride (2 equiv.) and was stirred for overnight. The reaction mixture was filtered and the filtrate was concentrated in vacuo. The residue was purified by flash column chromatography on silica gel to afford the $\overline{\text{N}}$Boc product as a solid, which was treated with 30% TFA in CH$_2$Cl$_2$ for 2 h. Excess trifluoroacetic acid and solvent were removed by evaporation. The residue was dissolved in a small amount of water, which was washed with ether and lyophilized.

Example 11

N$_\alpha$-(4S)-{[4-Amino-5-(3-amino)phenylamino]pentyl}-N'-nitroguanidine (15). This compound was prepared as described above using $N^a$-(tert-butoxycarbonyl)-L-nitroargininal (500 mg, 1.66 mmol) and (3-aminophenyl)carbamic acid tert-butyl ester (514.9 mg, 2.49 mmol). The purification by flash column chromatography on silica gel (EtOAc:hexane=3:1) gave $N^a$-(tert-butoxycarbonyl)-(4S)-{[4-amino-5-(3-amino)phenylamino]pentyl}-N'-nitroguanidine (300 mg, 37%). Removal of the Boc-group yielded 170 mg of 6 (95%, purple solid): $^1$H NMR (500 MHz, $D_2O$) δ7.11 (t, J=8 Hz, 1H), 6.60 (d, J=8 Hz, 1H), 6.52 (d, J=8 Hz, 1H), 6.47 (s, 1H), 3.31 (m, 1H), 3.22 (m, 2H), 3.10 (brs, 2H), 1.41-1.73 (m, 4H). HRMS (ES) (m/z): M+H$^+$ calcd for $C_{12}H_{22}N_7O_2$ 296.1835, found 296.1846.

Example 12

N-(4S)-{[4-Amino-5-(4-amino)phenylamino]-pentyl}-N'-nitroguanidine (16). This compound was prepared as described above using $N^a$-(tert-butoxycarbonyl)-L-nitroargininal (500 mg, 1.66 mmol) and (4-aminophenyl)carbamic acid tert-butyl ester (515 mg, 2.49 mmol). The purification by flash column chromatography on silica gel (EtOAc: hexane 2:1) gave $N^a$-(tert-butoxycarbonyl)-(4S)-{[4-amino-5-(4-amino)phenylamino]pentyl}-N'-nitroguanidine (400 mg, 49%). Removal of Boc-group from 360 mg yielded 197 mg of 7 (92%, orange solid): $^1$H NMR (500 MHz, $D_2O$) □7.04 (d, J=8 Hz, 2), 6.65 (d, J=8 Hz, 2), 3.34 (m, 1H), 3.30 (m, 2H), 3.14 (brs, 2H), 1.40-1.81 (m, 4H). HRMS (ES) (m/z): M+H$^+$ calcd for $C_{12}H_{22}N_7O_2$ 296.1835, found 296.1848.

Example 13

N-(4S)-[4-Amino-5-(2-aminobenzylamino)pentyl]-N'-nitroguanidine (17). This compound was prepared as described above using $N^a$-(tert-butoxycarbonyl)-L-nitroargininal (359 mg, 1.19 mmol), (2-aminomethyl)aniline (204 μl, 2.49 mmol). The residue was purified by flash column chromatography on silica gel ($CH_2Cl_2$:MeOH=3:2) to afford $N^□$-(tert-butoxycarbonyl)-(4S)-{4-amino-5-[(2-amino)benzylamino]-pentyl}-N'-nitroguanidine (270 mg, 56%) as a white solid. Removal of the Boc-group(30% TFA) gave a yellow foam (204 mg, 95% yield): $^1$H NMR (400 MHz, $D_2O$) δ7.57 (m, 2H), 7.46 (d, J=3.6 Hz, 1H), 7.29 (m, 1H), 3.44 (m, 1H), 3.31 (m, 2H), 3.17 (m, 2H), 1.46-1.90 (m, 4H). HRMS (ES) (m/z): M+H$^+$ calcd for $C_{13}H_{23}N_7O_2$ 310.1991, found 310.1920.

Example 14

N-(4S)-[4-Amino-5-(3-aminobenzylamino)pentyl]-N'-nitroguanidine (18). This compound was prepared as described above using $N^□$-(tert-butoxycarbonyl)-L-nitroargininal (500 mg, 1.66 mmol), (3-aminomethyl)aniline (284 μl, 2.49 mmol). The residue was purified by flash column chromatography on silica gel ($CH_2Cl_2$:MeOH=3:2) to afford $N^□$-(tert-butoxycarbonyl)-(4S)-[4-amino-5-(2-aminobenzylamino)pentyl]-N'-nitroguanidine (400 mg, 58.9%) as a white solid. Removal of Boc-group gave a light brown foam of 9 (278 mg, 92% yield): $^1$H NMR (500 MHz, $D_2O$) δ7.23 (m, 2H), 7.18 (brs, 1H), 7.13 (d, J=3 Hz, 1H), 4.01 (s, 2H), 3.39 (q, J=6 Hz, 1H), 3.12 (d, J=5.5 Hz, 2H), 2.93 (brs, 2H), 1.25-1.65 (m, 4H). HRMS (ES) (m/z): M+H$^+$ calcd for $C_{13}H_{23}N_7O_2$ 310.1991, found 310.2008.

Example 15

N-(4S)-[4-Amino-5-(4-aminobenzylamino)pentyl]-N'-nitroguanidine (19). This compound was prepared as described above using $N^a$-(tert-butoxycarbonyl)-L-nitroargininal (500 mg, 1.66 mmol), (4-aminomethyl)aniline (284 μl, 2.49 mmol). The residue was purified by flash column chromatography on silica gel ($CH_2Cl_2$:MeOH=3:2) to afford $N^a$-(tert-butoxycarbonyl)-(4S)-[4-amino-5-(2-aminobenzylamino) pentyl]-N-nitroguanidine (410 mg, 62%) as a white solid. An aliquot of 304 mg was treated with 30% TFA in $CH_2Cl_2$ to give 19 (204 mg, 89%, brown solid): $^1$H NMR (500 MHz, $D_2O$) δ7.43 (d, J=8.5 Hz, 2H), 7.28 (d, J=8.5 Hz, 2H), 4.16 (s, 2H), 3.52 (q, J=5.5 Hz, 1H), 3.26 (d, J=5.5 Hz, 2H), 3.10 (brs, 2H), 1.45-1.73 (m, 4H). HRMS (ES) (m/z): M+H$^+$ calcd for $C_{13}H_{23}N_7O_2$ 310.1991, found 310.1992.

Example 16

N-(4S)-{[4-Amino-5-(2-aminophenyl)ethylamino]pentyl}-N'-nitroguanidine (20). This compound was prepared as described above using $N^a$-(tert-butoxycarbonyl)-L-nitroargininal (400 mg, 1.32 mmol) and 2-(2-aminoethyl) aniline (361 mg, 2.65 mmol). The purification by flash column chromatography on silica gel ($CH_2Cl_2$:MeOH=1:1) gave $N^□$-(tert-butoxycarbonyl)-(4S)-{[4-amino-5-(2-aminophenyl)ethylamino]pentyl}-N'-nitroguanidine (415 mg, 74%). Removal of the Boc-group yielded 282 mg of 20 (89%, brown solid): $^1$H NMR (500 MHz, $D_2O$) δ7.26 (m, 4H), 3.53 (m, 1H), 3.26 (m, 4H), 3.12 (brs, 2H), 2.95 (t, J=6.8 MHz, 2H), 1.36-1.80 (m, 4H). HRMS (ES) (m/z): M+H$^+$ calcd for $C_{14}H_{26}N_7O_2$ 324.2148, found 324.2151.

Example 17

N-(4S)-{[4-Amino-5-(3-aminophenyl)ethylamino]pentyl}-N'-nitroguanidine (21). This compound was prepared as described above using $N^a$-(tert-butoxycarbonyl)-L-nitroargininal (400 mg, 1.32 mmol) and 3-(2-aminoethyl) aniline (361 mg, 2.65 mmol). The purification by flash column chromatography on silica gel ($CH_2Cl_2$:MeOH=1:1) gave $N^a$-(tert-Butoxycarbonyl)-(4S)-[4-amino-5-(3-aminophenyl)-ethylamino)-pentyl]-N'-nitroguanidine (250 mg, 45%). Removal of the Boc-group yielded 189 mg of 21 (99%, brown solid): $^1$H NMR (400 MHz, $D_2O$) δ7.30 (d, J=7.2 Hz, 1H), 7.21 (d, J=7.2 Hz, 1H), 7.11 (m, 2H), 3.49 (m, 1H), 3.20 (m, 4H), 3.11 (brs, 2H), 2.90 (t, J=7.2 MHz, 2H), 1.33-1.77 (m, 4H). HRMS (ES) (m/z): M+H$^+$ calcd for $C_{14}H_{26}N_7O_2$ 324.2148, found 324.2147.

Example 18

N-(4S)-{[4-Amino-5-(4-aminophenyl)ethylamino]pentyl}-N'-nitroguanidine (22). This compound was prepared as described above using $N^a$-(tert-butoxycarbonyl)-L-nitroargininal (500 mg, 1.66 mmol) and 4-(2-aminoethyl) aniline (338 μL, 2.49 mmol). The purification by flash column chromatography on silica gel ($CH_2Cl_2$:MeOH=2:1) gave $N^a$-(tert-butoxycarbonyl)-(4S)-[4-amino-5-(4-aminophenyl) ethylamino)pentyl]-N'-nitroguanidine (380 mg, 54%). Removal of the Boc-group yielded 218 mg of 22 (95%, yellow solid): $^1$H NMR (500 MHz, $D_2O$) δ7.28 (d, J=8 Hz, 2H), 7.21 (d, J=8 Hz, 2H), 3.53 (m, 1H), 3.24 (m, 4H), 3.15 (brs, 2H), 2.94 (t, J=7.5 MHz, 2H), 1.43-1.77 (m, 4H). HRMS (ES) (m/z): M+H$^+$ calcd for $C_{14}H_{26}N_7O_2$ 324.2148, found 324.2150. Anal Calcd for $C_{14}H_{25}N_7O_2$·3TFA·$H_2O$: C, 35.15, H, 4.42, N, 14.35; Found: C, 35.65, H, 4.25, N, 14.30.

Example 19

$N^a$-(4S)-{4-Amino-5-[(2-aminomethyl)phenylamino]pentyl}-N'-nitroguanidine (23). This compound was prepared as described above using N$^\alpha$-(tert-butoxycarbonyl)-L-nitroargininal (200 mg, 0.73 mmol) and (2-aminobenzyl)carbamic acid tert-butyl ester (324 mg, 1.46 mmol). The purification by flash column chromatography on silica gel (EtOAc:hexane=2:1) gave N$^\alpha$-(tert-butoxycarbonyl)-(4S)-{4-amino-5-[(3-aminomethyl)phenylamino]pentyl}-N'-nitroguanidine (160 mg, 43%). Removal of the Boc-group yielded 92.3 mg of 23 (95%, orange solid): $^1$H NMR (400 MHz, D$_2$O) δ7.55 (m, 2H), 7.46 (m, 1H), 7.27 (m, 1H), 3.63 (m, 1H), 3.31 (m, 2H), 3.23 (m, 4H), 1.40-1.88 (m, 4H). HRMS (ES) (m/z): M+H$^+$ calcd for C$_{13}$H$_{23}$N$_7$O$_2$ 310.1991, found 310.1931.

Example 20

N-(4S)-{4-Amino-5-[(3-aminomethyl)phenylamino]pentyl}-N'-nitroguanidine (24). This compound was prepared as described above using N$^\alpha$-(tert-butoxycarbonyl)-L-nitroargininal (458.5 mg, 1.52 mmol) and (3-aminobenzyl)carbamic acid tert-butyl ester (675 mg, 3.04 mmol). The purification by flash column chromatography on silica gel (EtOAc:hexane=1:1) gave N$^\alpha$-(tert-butoxycarbonyl)-(4S)-{4-amino-5-[(3-aminomethyl)phenylamino]pentyl}-N'-nitroguanidine (320 mg, 41%). Removal of the Boc-group yielded 120 mg of 24 (62%, brown solid): $^1$H NMR (400 MHz, D$_2$O) δ7.18 (t, J=7.5 Hz, 1H), 6.79 (m, 3H), 3.91 (s, 2H), 3.55 (m, 1H), 3.37 (m, 2H), 3.09 (m, 2H), 1.36-1.82 (m, 4H). HRMS (ES) (m/z): M+H$^+$ calcd for C$_{13}$H$_{23}$N$_7$O$_2$ 310.1991, found 310.1992. Anal Calcd for C$_{13}$H$_{23}$N$_7$O$_2$.3TFA2H$_2$O: C, 33.19, H, 4.40, N, 14.26; Found: C, 33.62, H, 4.38, N, 14.19.

Example 21

N-(4S)-{4-Amino-5-[(4-aminomethyl)phenylamino]pentyl}-N'-nitroguanidine (25). This compound was prepared as described above using N$^\alpha$-(tert-butoxycarbonyl)-L-nitroargininal (500 mg, 1.66 mmol) and (4-aminobenzyl)carbamic acid tert-butyl ester (569 mg, 2.49 mmol). The purification by flash column chromatography on silica gel (EtOAc:hexane=2:1) gave N$^\alpha$-(tert-butoxycarbonyl)-(4S)-{4-amino-5-[(4-aminomethyl)phenylamino]pentyl}-N'-nitroguanidine (390 mg, 46%). Removal of the Boc-group yielded 234 mg of 25 (99%, pale yellow solid): $^1$H NMR (400 MHz, D$_2$O) δ7.12 (d, J=8 Hz, 2), 6.65 (d, J=8 Hz, 2), 3.89 (s, 2H), 3.36 (m, 1H), 3.29 (m, 2H), 3.14 (brs, 2H), 1.36-1.62 (m, 4H). HRMS (ES) (m/z): M+H$^+$ calcd for C$_{13}$H$_{23}$N$_7$O$_2$ 310.1991, found 310.1992.

Example 22

N-(4S)-{4-Amino-5-[2-(2-aminoethyl)phenylamino]pentyl}-N'-nitroguanidine (26). This compound was prepared as described above using N$^\alpha$-(tert-butoxycarbonyl)-L-nitroargininal (463.5 mg, 1.53 mmol) and [2-(2-aminophenyl)ethyl]carbamic acid tert-butyl ester (544 mg, 2.30 mmol). The purification by flash column chromatography on silica gel (EtOAc:hexane=2:1) gave N$^\alpha$-(tert-butoxycarbonyl)-(4S)-{4-amino-5-[2-(2-aminoethyl)phenylamino]pentyl}-N'-nitroguanidine (300 mg, 38%). Removal of the Boc-group yielded 176 mg of 26 (95%, brown solid): $^1$H NMR (400 MHz, D$_2$O) δ7.06 (t, J=6.8 Hz, 1H), 6.94 (d, J=6.8 Hz, 1H), 6.60 (m, 2H), 3.37 (m, 1H), 3.26 (m, 2H), 3.10 (brs, 2H), 3.04 (t, J=7.2 Hz, 2), 2.72 (t, J=7.2 Hz, 2H), 1.38-1.78 (m, 4H). HRMS (ES) (m/z): M+H$^+$ calcd for C$_{14}$H$_{26}$N$_7$O$_2$ 324.2148, found 324.2137. Anal Calcd for C$_{14}$H$_{25}$N$_7$O$_2$.3TFA.H$_2$O: C, 35.15, H, 4.42, N, 14.35; Found: C, 35.59, H, 4.32, N, 14.41.

Example 23

N-(4S)-{4-Amino-5-[3-(2-aminoethyl)phenylamino]pentyl}-N'-nitroguanidine (27). This compound was prepared as described above using N$^\alpha$-(tert-butoxycarbonyl)-L-nitroargininal (433 mg, 1.43 mmol) and [3-(2-aminophenyl)ethyl]carbamic acid tert-butyl ester (508 mg, 2.15 mmol). The purification by flash column chromatography on silica gel (EtOAc:hexane=2:1) gave N$^\alpha$-(tert-butoxycarbonyl)-(4S)-{4-amino-5-[3-(2-aminoethyl)phenylamino]pentyl}-N'-nitroguanidine (314 mg, 42%). Removal of the Boc-group yielded 174 mg of 27 (90%, brown solid): $^1$H NMR (400 MHz, D$_2$O) δ7.07 (t, J=7.6 Hz, 1H), 6.59 (m, 3H), 3.55 (m, 1H), 3.45 (m, 2H), 3.31 (m, 2H), 3.09 (m, 4H), 1.34-1.74 (m, 4H). HRMS (ES) (m/z): M+H$^+$ calcd for C$_{14}$H$_{26}$N$_7$O$_2$ 324.2148, found 324.2137.

Example 24

N-(4S)-{4-Amino-5-[4-(2-aminoethyl)phenylamino]pentyl}-N'-nitroguanidine (28). This compound was prepared as described above using N$^\alpha$-(tert-butoxycarbonyl)-L-nitroargininal (477 mg, 1.58 mmol) and [4-(2-amino-phenyl)ethyl]carbamic acid tert-butyl ester (560 mg, 2.37 mmol). The purification by flash column chromatography on silica gel (EtOAc:hexane=2:1) gave N$^\alpha$-(tert-butoxycarbonyl)-(4S)-{4-amino-5-[4-(2-aminoethyl)phenylamino]pentyl}-N'-nitroguanidine (300 mg, 36%). Removal of the Boc-group yielded 176 mg of 28 (95%, light brown solid): $^1$H NMR (500 MHz, D$_2$O) 7.01 (d, J=8 Hz, 2H), 6.64 (d, J=8 Hz, 2H), 3.60 (m, 1H), 3.49 (m, 1H), 3.29 (m, 3H), 3.15 (m, 2H), 2.72 (t, J=7.5 Hz, 2H), 1.42-1.81 (m, 4H). HRMS (ES) (m/z): M+H$^+$ calcd for C$_{14}$H$_{26}$N$_7$O$_2$ 324.2148, found 324.2154.

Example 25

N-(4S)-{4-Amino-5-[(pyridin-2-yl)methyl]aminopentyl}-N'-nitroguanidine (29). This compound was prepared as described above using N$^\alpha$-(tert-butoxycarbonyl)-L-nitroargininal (400 mg, 1.32 mmol), 1-(pyridin-2-yl)methylamine (204.8 μL, 1.98 mmol). The residue was purified by flash column chromatography on silica gel (EtOAc:MeOH=1:1) to afford N$^\alpha$-(tert-butoxycarbonyl)-(4S)-{4-amino-5-[(pyridin-2-ylmethyl)amino]pentyl}-N'-nitroguanidine (340 mg, 65%) as a yellow solid. Removal of the Boc-group gave 29 as a pale yellow foam (251 mg, 99%, brown solid): $^1$H NMR (500 MHz, D$_2$O) δ8.64 (d, J=5.5 Hz, 1H), 8.37 (t, J=8 Hz, 1H), 7.91 (d, J=8 Hz, 1H), 7.83 (t, J=6.5 Hz, 1H), 4.51 (s, 2H), 3.57 (m, 1H), 3.37 (m, 2H), 3.12 (brs, 2H), 1.42-1.80 (m, 4H). HRMS (ES) (m/z): M+H$^+$ calcd for C$_{12}$H$_{22}$N$_7$O$_2$ 296.1385, found 296.1837.

Example 26

N-(4S)-{4-Amino-5-[(pyridin-3-yl)methyl]amino]pentyl}-N'-nitroguanidine (30). This compound was prepared as described above using N$^\alpha$-(tert-butoxycarbonyl)-L-nitroargininal (400 mg, 1.32 mmol), 1-(pyridin-3-yl)methylamine (202 μL, 1.98 mmol). The residue was purified by flash column chromatography on silica gel (EtOAc:MeOH=1:1) to afford N$^\alpha$-(tert-butoxycarbonyl)-(4S)-{4-amino-5-[(pyridin-3-ylmethyl)amino]pentyl}-N'-nitroguanidine (300 mg, 58%) as a yellow solid. Removal of the Boc-group gave 30 as a greenish yellow foam (217 mg, 97%): $^1$H NMR (500 MHz, D$_2$O) δ8.78 (brs, 1H), 8.68 (d, J=5.5 Hz, 1H), 8.56 (d, J=7.5 Hz, 1H), 7.96 (t, J=7.5 Hz, 1H), 4.39 (s, 2H), 3.55 (m, 1H), 3.36 (m, 2H), 3.08 (brs, 2H), 1.39-1.82 (m, 4H). HRMS (ES) (m/z): M+H⁺ calcd for $C_{12}H_{22}N_7O_2$ 296.1385, found 296.1839. Anal Calcd for $C_{12}H_{21}N_7O_2 \cdot 3TFA2H_2O$: C, 32.10, H, 4.19, N, 14.56; Found: C, 31.62, H, 4.16, N, 14.47.

Example 27

N-(4S)-{4-Amino-5-[(pyridin-4-yl)methyl]aminopentyl}-N'-nitroguanidine (31). This compound was prepared as described above using $N^\alpha$-(tert-butoxycarbonyl)-L-nitroargininal (420 mg, 1.39 mmol), 1-(pyridin-4-yl)methylamine (211 μL, 2.09 mmol). The residue was purified by flash column chromatography on silica gel (EtOAc:MeOH=5:2) to afford $N^\alpha$-(tert-butoxycarbonyl)-(4S)-{4-amino-5-[(pyridin-4-ylmethyl)amino pentyl}-N'-nitroguanidine (419 mg, 76%) as a yellow solid. Removal of the Boc-group gave 31 as a orange yellow foam (310 mg, 99%): ¹H NMR (500 MHz, D₂O) δ8.72 (d, J=6 Hz, 2H), 8.01 (d, J=6 Hz, 2H), 4.50 (s, 2H), 3.62 (m, 1H), 3.43 (m, 2H), 3.15 (brs, 2H), 1.46-1.83 (m, 4H). HRMS (ES) (m/z): M+H⁺ calcd for $C_{12}H_{22}N_7O_2$ 296.1385, found 296.1848.

Example 28

N-(4S)-{4-Amino-5-[(2-pyridin-2-yl)ethyl]aminopentyl}-N'-nitroguanidine (32). This compound was prepared as described above using $N^\alpha$-(tert-butoxycarbonyl)-L-nitroargininal (415 mg, 1.37 mmol), 2-(pyridin-2-yl)ethylamine (190 μL, 1.51 mmol). The residue was purified by flash column chromatography on silica gel (EtOAc:MeOH=1:1) to afford $N^\alpha$-(tert-butoxycarbonyl)-(4S)-{4-amino-5-[(2-pyridin-2-yl)ethyl]amino pentyl}-N'-nitroguanidine (400 mg, 71%) as a yellow solid. Removal of the Boc-group gave 32 as a light brown foam (296 mg, 98%): ¹H NMR (500 MHz, D₂O) δ8.38 (d, J=5.5 Hz, 1H), 8.21 (t, J=8 Hz, 1H), 7.66 (d, J=8 Hz, 1H), 7.63 (m, 1H), 3.41 (m, 1H), 3.30 (m, 2H), 3.24 (m, 2H), 3.16 (m, 2H), 2.95 (brs, 2H), 1.26-1.62 (m, 4H). HRMS (ES) (m/z): M+H⁺ calcd for $C_{13}H_{24}N_7O_2$ 310.1991, found 310.1995.

Example 29

N-(4S)-{4-Amino-5-[(2-pyridin-3-yl)ethyl]aminopentyl}-N'-nitroguanidine (33). This compound was prepared as described above using $N^\alpha$-(tert-butoxycarbonyl)-L-nitroargininal (460 mg, 1.52 mmol), 2-(pyridin-3-yl)ethylamine dihydrobromide salt (509 mg, 1.82 mmol). The residue was purified by flash column chromatography on silica gel (EtOAc:MeOH=1:1) to afford $N^\alpha$-(tert-butoxycarbonyl)-(4S)-{4-amino-5-[(2-pyridin-3-yl)ethyl]aminopentyl}-N'-nitroguanidine (404 mg, 65%) as a yellow solid. Removal of the Boc-group gave 33 as a pale yellow foam (290 mg, 95%): ¹H NMR (500 MHz, D₂O) 6849 (brs, 1H), 8.45 (d, J=4.5 Hz, 1H), 8.30 (d, J=6.5 Hz, 1H), 7.77 (ddd, J=4.5, 6 Hz, 1H), 3.46 (m, 1H), 3.25 (m, 2H), 3.20 (m, 2H), 3.07 (m, 2H), 3.02 (brs, 2H), 1.35-1.71 (m, 4H). HRMS (ES) (m/z): M+H⁺ calcd for $C_{13}H_{24}N_7O_2$ 310.1991, found 310.1995.

Example 30

N-(4S)-{4-Amino-5-[(2-pyridin-4-yl)ethylamino]pentyl}-N'-nitroguanidine (34). This compound was prepared as described above using $N^\alpha$-(tert-butoxycarbonyl)-L-nitroargininal (400 mg, 1.32 mmol), 2-(pyridin-4-yl)ethylamine (249 μL, 1.98 mmol). The residue was purified by flash column chromatography on silica gel (EtOAc:MeOH=1:1) to afford $N^\alpha$-(tert-butoxycarbonyl)-(4S)-{4-amino-5-[(2-pyridin-4-yl)ethyl amino]pentyl}-N'-nitroguanidine (400 mg, 74%) as a yellow solid. Removal of the Boc-group gave 34 as a white foam (287 mg, 95%): ¹H NMR (500 MHz, D₂O) δ845 (d, J=6 Hz, 1H), 7.73 (d, J=6 Hz, 2H), 3.49 (q, J=6 Hz, 1H), 3.30 (m, 2H), 3.21 (m, 1H), 3.15 (t, J=7.5 Hz, 2H), 3.03 (brs, 2H), 1.33-1.76 (m, 4H). HRMS (ES) (m/z): M+H⁺ calcd for $C_{13}H_{24}N_7O_2$ 310.1991, found 310.1994.

Example 31

2-(2-Aminoethyl)aniline (39). To a solution of (2-nitrophenyl)acetonitrile (3 g, 18.5 mmol) was added dropwise a 1 M BH₃-THF solution (125 mL) at 0° C. After 4 h of stirring at 25° C., 6N HCl solution (125 mL) was added to the reaction mixture at 0° C. After evaporation of the organic solvent in vacuo, the aqueous phase was basified with 4N NaOH solution to pH 10. Then the product was extracted with EtOAc and the organic phase was dried over MgSO₄ and concentrated in vacuo. A brown liquid (41, 2 g, 10.8 mmol) was isolated. Without further purification, it was mixed with $SnCl_2 \cdot 2H_2O$ (13.57 g, 60.2 mmol) and absolute ethanol (20 mL). The suspension was heated at 70° C. under nitrogen. After being stirred for 30 min, the starting material disappeared, the solution was allowed to cool, then poured into ice (100 g). The pH was made slightly basic (pH 8) by the addition of a 5% aqueous NaHCO₃ solution, and the resulting basic mixture was stirred for 1 h. The precipitate was extracted with ethyl acetate (100 mL×3). The extract was washed with water (50 mL×3) and dried over MgSO₄. The product was obtained in a yield of 52% (1.3 g, brown liquid, over two steps) after evaporation of the solvent: ¹H NMR (400 MHz, CD₃OD) δ6.97 (t, J=7.2 Hz, 2H), 6.72 (d, J=7.2 Hz, 2H), 6.64 (t, J=7.2 Hz, 1H), 2.82 (t, J=7.2 Hz, 2H), 2.66 (t, J=7.2 Hz, 2H). HRMS (EI) m/z (M⁺) calcd for $C_8H_{12}N_2$ 136.1000, found 136.1002.

Example 32

3-(2-Aminoethyl)aniline (40). This compound was prepared as described above using (3-nitrophenyl)acetonitrile (2.2 g, 13.6 mmol). Evaporation of the solvent gave the product in a yield of 81% (1.5 g, brown liquid, over two steps): ¹H NMR (400 MHz, CD₃OD) δ7.02 (t, J=7.2 Hz, 1H), 6.59 (m, 2H), 6.56 (m, 1H), 2.84 (t, J=7.2 Hz, 2H), 2.64 (t, J=7.2 Hz, 2H). HRMS (EI) m/z (M⁺) calcd for $C_8H_{12}N_2$ 136.1000, found 136.0980.

Example 33

(3-Aminophenyl)carbamic acid tert-butyl ester (45). A solution of di-tert-butyl-dicarbonate (2 g, 9.16 mmol, 1 equiv.) in dioxane (25 mL) was added over a period of 30 min to a solution of 1,3-phenylenediamine (2 g, 18.5 mmol, 2 equiv.) in dioxane (25 mL). The mixture was allowed to stir for 22 h, and the solvent was removed using a rotary evaporator. The residue was purified by flash column chromatography on silica gel (EtOAc:hexane=2:1) to afford 1.7 g of product (89% based on dicarbonate) as a peach color solid: ¹H NMR (500 MHz, CDCl₃) δ7.11 (t, J=8 Hz, 1H), 6.60 (d, J=8 Hz, 1H), 6.52 (t, J=8 Hz, 1H), 6.47 (s, 1H), 4.79 (s, 1H), 1.44 (s, 9H). HRMS (EI) m/z (M⁺) calcd for $C_{11}H_{16}N_2O_2$ 208.1211, found 208.1201.

Example 34

(2-Aminobenzyl)carbamic acid tert-butyl ester (47). This compound was prepared as described above using di-tertbutyl-dicarbonate (2 g, 9.16 mmol) and 2-aminomethyl-aniline (2 g, 18.5 mmol). The residue was purified by flash column chromatography on silica gel (EtOAc:hexane=2:1) to afford 1.5 g of product (79% based on dicarbonate) as a light yellow solid: $^1$H NMR (400 MHz, CDCl$_3$) δ7.10 (t, J=7.6 Hz, 1H), 7.02 (d, J=6.8 Hz, 1H), 6.67 (m, 2H), 4.80 (s, 1H), 1.44 (s, 9H). HRMS (EI) m/z (M$^+$) calcd for C$_{12}$H$_{18}$N$_2$O$_2$ 222.1369, found 222.1357.

Example 35

(3-Aminobenzyl)carbamic acid tert-butyl ester (48). This compound was prepared as described above using di-tert-butyl-dicarbonate (0.89 g, 4.07 mmol) and 3-aminomethyl-aniline (1 g, 8.18 mmol). The residue was purified by flash column chromatography on silica gel (EtOAc:hexane=2:1) to afford 0.95 g of brown liquid (quantitative yield): $^1$H NMR (400 MHz, CDCl$_3$) δ7.08 (t, J=7.6 Hz, 1H), 6.64 (d, J=7.6 Hz, 1H), 6.58 (m, 2H), 4.91 (s, 2H), 1.45 (s, 9H). HRMS (EI) m/z (M$^+$) calcd for C$_{12}$H$_{18}$N$_2$O$_2$ 222.1369, found 222.1357.

Example 36

[(2-Aminophenyl)ethyl]carbamic acid tert-butyl ester (50). This compound was prepared as described above using di-tert-butyl-dicarbonate (0.3 g, 2.2 mmol) and 2-(2-aminoethyl)aniline (481 mg, 2.2 mmol). The product was obtained as a pale yellow solid in a quantitative yield (544 mg): $^1$H NMR (400 MHz, CD$_3$OD) δ6.97 (t, J=7.2 Hz, 2H), 6.71 (d, J=8 Hz, 1H), 6.63 (t, J=7.2 Hz, 1H), 3.18 (t, J=8 Hz, 2H), 2.67 (t, J=8 Hz, 2H), 1.43 (s, 9H). HRMS (EI) m/z (EI) calcd for C$_{13}$H$_{20}$N$_2$O$_2$ 236.1524, found 236.1537.

Example 37

[(3-Aminophenyl)ethyl]carbamic acid tert-butyl ester (51). This compound was prepared as described above using di-tert-butyl-dicarbonate (401 mg, 1.84 mmol) and 3-(2-aminoethyl)aniline (401 mg, 1.84 mmol). The residue was purified by flash column chromatography on silica gel (EtOAc:hexane=2:1) to afford 508 mg of product (quantitative yield, yellow solid): $^1$H NMR (400 MHz, CD$_3$OD) δ☐7.00 (t, J=8 Hz, 1H), 6.58 (m, 3H), 3.21 (t, J=7.6 Hz, 2H), 3.63 (t, J=7.6 Hz, 2H), 1.42 (s, 9H). HRMS (EI) m/z (M$^+$) calcd for C$_{13}$H$_{20}$N$_2$O$_2$ 236.1524, found 236.1508.

Example 38

[(4-Aminophenyl)ethyl]carbamic acid tert-butyl ester (52). This compound was prepared as described above using di-tert-butyl-dicarbonate (1 g, 7.34 mmol) and 4-(2-aminoethyl)aniline (0.8 g, 3.67 mmol). The product was obtained in a yield of 98% (850 mg, pale yellow solid): $^1$H NMR (400 MHz, CDCl$_3$) δ6.96 (d, J=8.4 Hz, 2H), 6.62 (d, J=8.4 Hz, 2H), 3.29 (t, J=6.4 Hz, 2H), 2.66 (t, J=6.4 Hz, 2H), 1.43 (s, 9H). HRMS (EI) m/z (M$^+$) calcd for C$_{13}$H$_{20}$N$_2$O$_2$ 236.1524, found 236.1555.

Example 39

Synthesis of the compositions of examples 40-45 was implemented on solid-phase. The substituted proline derivatives were prepared following published methodology (Gomez-Vidal, J. A.; Silverman, R. B. Short, Highly Efficient Syntheses of Protected 3-Azido- and 4-Azidoproline and Their Precursors. *Org. Lett.* 2001, 3, 2481-2484. b) Gomez-Vidal, J. A.; Forrester, M. T.; Silverman, Richard B. Mild and Selective Sodium Azide Mediated Cleavage of p-Nitrobenzoic Esters. *Org. Lett.* 2001, 3, 2477-2479) or obtained from commercial sources. Enzymatic activity was demonstrated using techniques and procedures known in the art and/or as otherwise referenced herein. Likewise, standard assay techniques were used to demonstrate utility of this aspect of the invention.

Example 40

Figure 11:
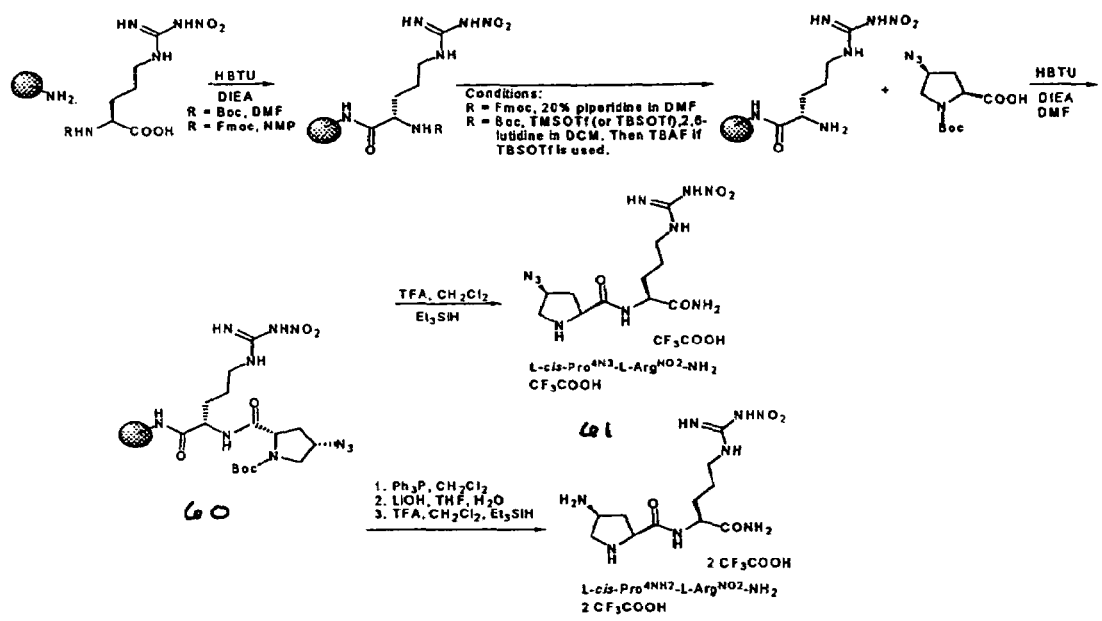
FIGS. 11-16 represent, without limitation, synthetic routes of the sort available for several compositions provided in FIG. 10 and/or elsewhere herein. Several such representative compositions show use of various protecting group strategies and/or compositions isolated as acid salts, use of which are also in accordance with this invention.

Dipeptide derivatives with 4-azido- and 4-amino-L- and D-proline at the N-terminus Various compounds in accordance with this example can be obtained as shown in FIG. 11. Rink amide resin was loaded with Fmoc- or Boc-protected L-Arg$^{NO2}$ or D-Arg$^{NO2}$. Fmoc deprotection was carried out with a 20% piperidine solution in DMF. Boc deprotection was carried out using a modified Burgess methodology. (Zhang, A. J.; Russell, D. H.; Zhu, J.; Burgess, K. A Method for Removal of N—BOC Protecting Groups from Substrates on TFA-sensitive Resins. *Tetrahedron Lett.* 1998, 39, 7439-7442.) Two equivalents of TBSOTf were used to effect Boc deprotection at room temperature instead of an excess of TMSOTf. A further modification using 2 equiv. of TMSOTf instead of TBSOTf and TBAF was introduced to avoid the two steps N-Boc deprotection. Parallel solid phase synthesis was carried out to obtain all the stereoisomers of 60 from L- or D-Arg$^{NO2}$ and protected L- or D-cis- or trans-4-azido-proline. Part of the resin 60 was cleaved to obtain all the stereisomers of compound 61. The azide group in 60 was reduced to the amino group under Staudinger conditions. (Scriven, E. F. V.; Turnbull, K. Azides: Their Preparation and Synthetic Uses. *Chem. Rev.* 1988, 88, 297-368) All the stereoisomers of compound 62 were obtained following the synthetic procedure described in FIG. 3. The procedure of the example is general and has been followed for the synthesis of dipeptides derivatives with constrained mimics of L-Dbu at the N-terminal.

Example 41

Figure 12:
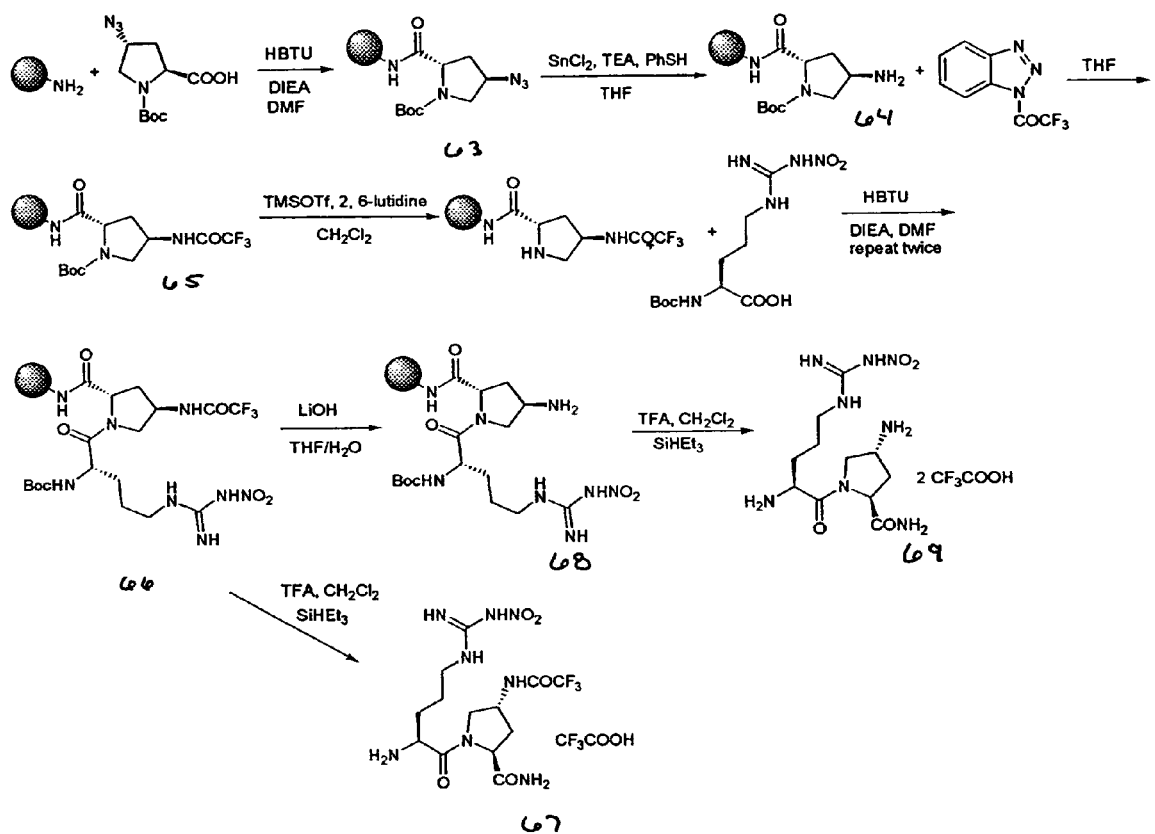

Dipeptide derivatives with 4-trifluoroacetamido- and 4-amino-L- and D-proline at the C-terminus The synthesis of dipeptides containing 4-amino proline derivatives at the C-terminus has been achieved on Rink resin (see FIG. 12). Triethylammonium tris(phenylthio)stannate was used to reduced the azide group in 63 to an amino group in 64. This reagent has been described as a very efficient reducing agent with a high chemoselectivity toward azides (Bartra, M.; Romea, P.; Urpi, F.; Vilarrasa, J. A Fast Procedure for the Reduction of Azides and Nitro Compounds Based on the Reducing Ability of Sn(SR)$_3^-$ Species. *Tetrahedron.* 1990, 46, 587-594), and has been applied successfully on solid phase using Rink resin or other resins. (Kim, J.; Bi, Y., Paikoff, S. J.; Schultz, P. G. The Solid Phase Synthesis of Oligoureas. *Tetrahedron Lett.* 1996, 37, 5305-5308.) Kick, E.; Ellman, J. A. Expedient Method for the Solid-Phase Synthesis of Aspartic Acid Protease Inhibitors Directed toward the Generation of Libraries. *J. Med. Chem.* 1995, 38, 1427-1430. b) Tortolani, D. R.; Biller, S. A. A Solid Phase Synthesis of Miconazole Analogs via an Iodoetherification Reaction. *Tetrahedron Lett.* 1996, 37, 5687-5690). After azide reduction the resultant amine is protected as a trifluoroacetamide 65 (a) Greene, T. W. and Wuts, P. G. M. *Protective Groups in Organic Synthesis*; John Wiley & Sons, Inc.: New York, 1999; p 556. b) Katritzky, A. R., Yang, B., Semenzin, D. (Trifluoroacetyl)benzotriazole: A Convenient Trifluoroacetylating Reagent. *J. Org. Chem.* 1997, 62, 726-728). This additional step is necessary because of the azide instability during N-Boc deprotection using TMSOTf. This is not a general occurrence because this reaction has been described previously with N-Boc deprotection in the presence of a secondary azide. (Nicolaou, K. C.; Koumbis, A. E.; Takayanagi, M.; Natarajan, S.; Jain, N. F.; Bando, T.; Li, H.; Hughes, R. Total Synthesis of Vancomycin-Part 3: Synthesis of the Aglycon. *Chem. Eur. J.* 1999, 5, 2622-2647)

The new protecting group should be orthogonal to Boc and stable to TMSOTf. It should also be eliminated using conditions that do not affect the Rink resin or the stereochemistry of the final dipeptide. (Trifluoroacetyl)benzotriazole has been described as a useful reagent for the introduction of this protecting group (a) Greene, T. W. and Wuts, P. G. M. *Protective Groups in Organic Synthesis*; John Wiley & Sons, Inc.: New York, 1999; p 556. b) Katritzky, A. R., Yang, B., Semenzin, D. (Trifluoroacetyl)benzotriazole: A Convenient Trifluoroacetylating Reagent. *J. Org. Chem.* 1997, 62, 726-728). Its deprotection is accomplished under basic conditions but its stability toward TMSOTf had not been investigated.

The dipeptide 66 was obtained after Boc deprotection and coupling reaction with Boc protected L- or D-Arg$^{NO2}$. Part of the resin 66 was cleaved to obtain dipepetide 67. All the stereisomers of compound 66 were obtained using parallel synthesis from the L- or D-cis- or trans-4-azidoproline and L- or D-Arg$^{NO2}$. Trifluoroacetamide 66 was deprotected using LiOH in THF and H$_2$O to obtain amine 68. This compound was cleaved from the resin to obtain dipeptide 69. All the stereoisomers of compound 69 were obtained as described in FIG. 12.

The synthetic procedures and methods of this example proved to be successful for the synthesis of various 4-aminoproline containing dipeptides at the C-terminus.

Example 42

Figure 13:
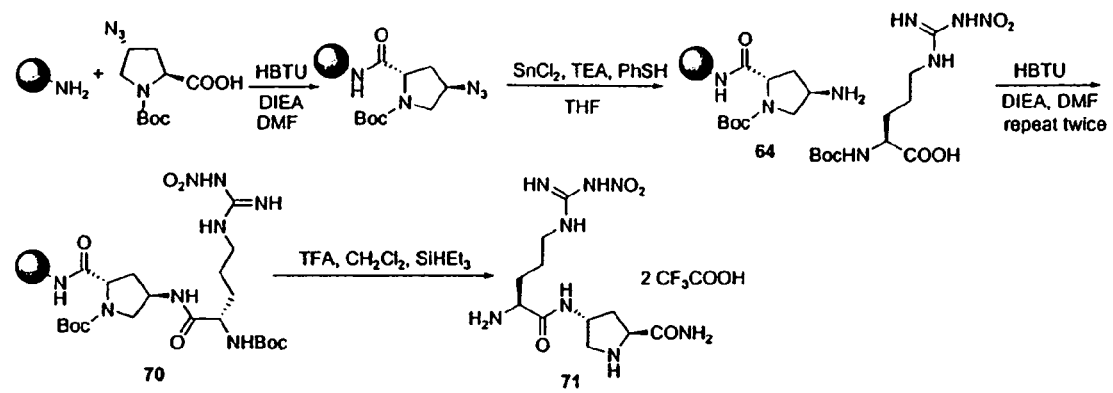

Nonnatural dipeptides containing L- or D-Arg$^{NO2}$ and 3-amino and 4-aminoproline derivatives A third family of dipeptides has been synthesized using the exocyclic nitrogen on the proline derivative to obtain the dipeptide bond (see FIG. 13). These structures can be described as conformationally restricted analogs of the lead compound but without a substituted peptide bond. Intermediate 64 is coupled to L- or D-Arg$^{NO2}$ to obtain dipeptide 70. This compound was cleaved from the resin to obtain 71. All the stereoisomers of 71 were obtained following the scheme of FIG. 13 from protected L- and D-cis- and trans-4-aminoproline.

Thirty-two compounds were synthesized following the schemes of FIGS. 11 and 12 and eight compounds were synthesized following the scheme of FIG. 13. All of these compounds were purified by solid phase extraction (SPE), and the final purity was determined by analytical HPLC and $^1$HNMR. A Luna column (Phenomenex, C18-2, 250*4.6 mm, 5U) was selected as the analytical column, and a rapid method was developed to analyze each sample.

Example 43

Figure 14:
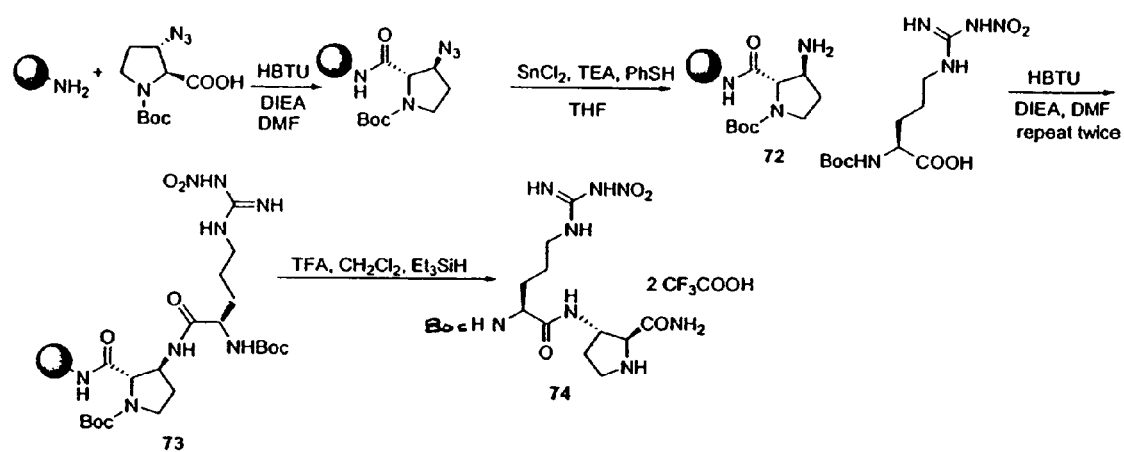

The synthetic procedure of example 42 was used starting from N-Boc-L-trans- and cis-4-azidoproline (see FIG. 14). N-Boc-L-Arg$^{NO2}$ was coupled to 72 to obtain dipeptide intermediate 73. This compound was cleaved from the resin to obtain 74. The cis isomer was also obtained starting from protected cis-azido-proline.

Example 44

Figure 15:
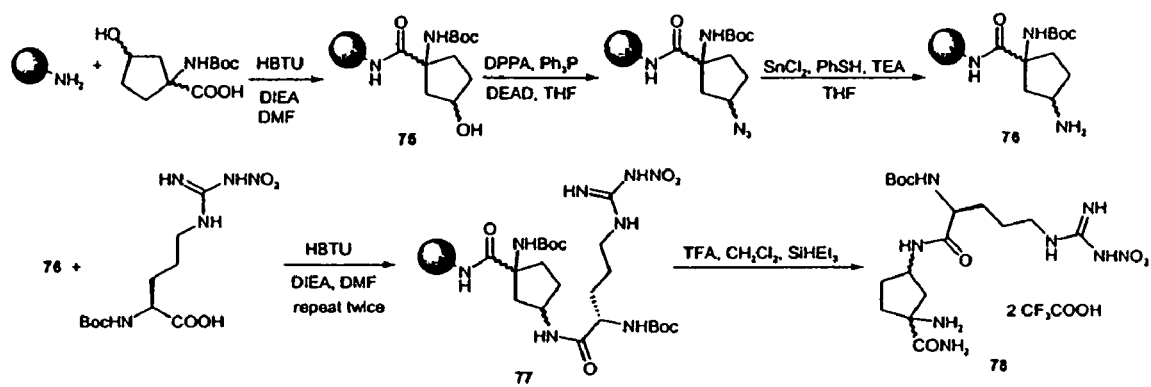

Synthesis of dipeptides from L-Arg$^{NO2}$ and N-Boc-amino-(3-hydroxycyclopentyl)carboxylic acid or N-Fmoc-amino-(3-hydroxycyclopentyl)carboxylic acid Rink amide resin was loaded with a racemic mixture of N-Boc-amino-(3-hydroxycyclopontyl)carboxylic acid using HBTU as a coupling reagent to give intermediate 75 (see FIG. 15). The hydroxy group in 75 was converted to an azido group under Mitsunobu conditions (Nicolaou, K. C.; Winssinger, N.; Vourloumis, D.; Ohshima, T.; Kim, S.; Pfefferkorn, J.; Xu, J.; Li, T. Solid and Solution Phase Synthesis and Biological Evaluation of Combinatorial Sarcodictyin Libraries. *J. Am. Chem. Soc.* 1998, 120, 10814-10826) and reduced to an amino group in 76. N-Boc-L-Arg$^{NO2}$ was coupled to give dipeptide 77 that was cleaved to obtain dipeptide 78 as a mixture of 4 diastereomers. This mixture was pre-purified using SPE and two fractions with two different diastereomers each were used for enzyme assays.

Example 45

Figure 16:
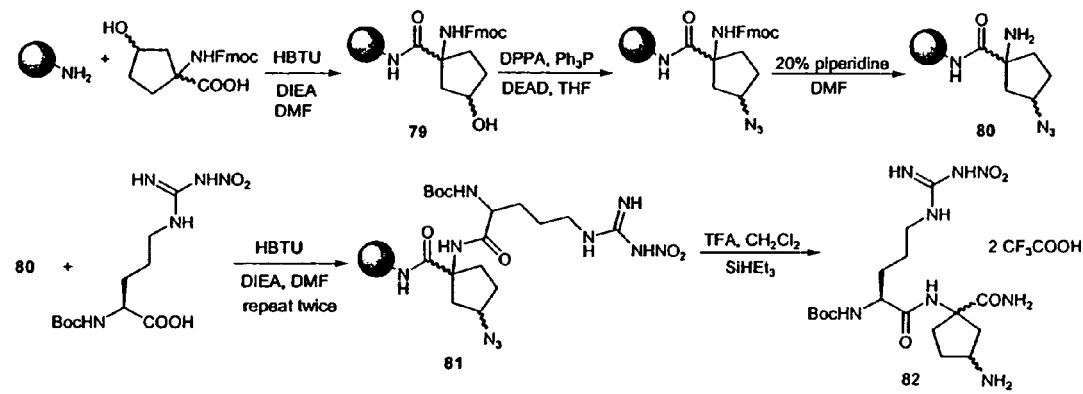
Figure 17:
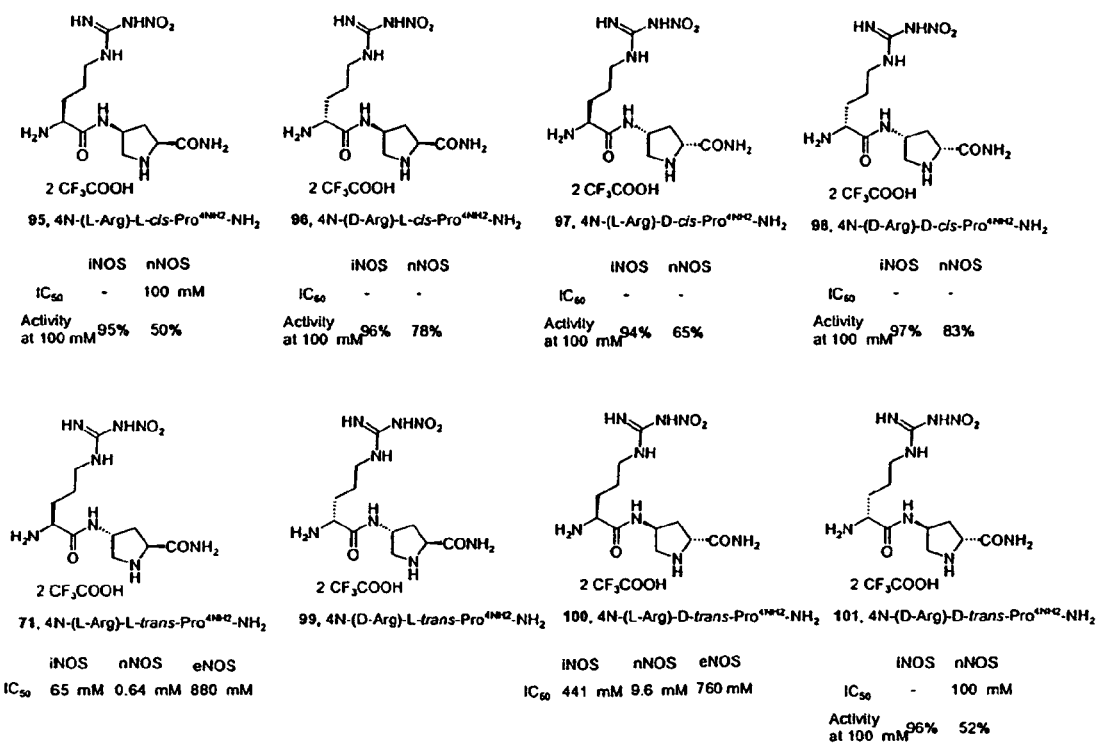
FIG. 17 compares NOS activities of several 4-amino proline coupled dipeptide derivatives, such derivatives examples only of various other compositions in accordance with this invention.

N-Fmoc-amino-(3-hydroxycyclopentyl)carboxylic acid was loaded as a racemic mixture on Rink amide resin to give 79 (see FIG. 16). The hydroxy group in 79 was converted to an azido group under Mitsunobu conditions and the Fmoc protecting group was removed using 20% piperidine in DMF to give 80. This intermediate was coupled to N-Boc-L-Arg$^{NO2}$ to obtain the dipeptide 81. After azide reduction under Staudinger conditions the compound was cleaved from the resin to give dipeptide 82 as a mixture of 4 diastereomers. This mixture was pre-purified using SPE before enzyme assays.

Example 46

Enzyme-activity of dipeptide analogs containing proline derivatives at the N- and the C-terminus.

Thirty-two derivatives containing proline derivatives at the N- and the C-terminus did not show activity at 100 μM against iNOS (IC$_{50}$>100 μM). Some compounds have an IC$_{50}$ value of 100 μM or less against nNOS (see Table 3 and Table 4).

TABLE 3 nNOS activities of the dipeptide analogs containing proline derivatives at the C-terminus.

| | Activity at 100 μM |
|---|---|
| 67 L-Arg$^{NO2}$-L-trans-Pro$^{4NHCOCF3}$-NH$_2$ | 41% |
| 69 L-Arg$^{NO2}$-L-trans-Pro$^{4NH2}$-NH$_2$ | 50% |
| 83 D-Arg$^{NO2}$-D-cis-Pro$^{4NH2}$-NH$_2$ | 56% |

Only three dipeptides analogs containing proline derivatives at the C-terminus exhibited some activity with nNOS at 100 μM (see Table 3 above). This supports the importance of a non-substituted peptide bond for the interaction with the enzyme (Huang, H.; Martasek, P.; Roman, L. J.; Silverman, R. B. Synthesis and evaluation of peptidomimetics as selective inhibitors and active site probes of nitric oxide synthases. *J. Med. Chem.* 2000, 43, 2938-2945).

Twelve dipeptide analogs containing proline derivatives at the N-terminus showed activity over nNOS at 100 μM (see Table 3). L-trans-Pro$^{4NH2}$-L-Arg$^{NO2}$-NH$_2$ is the most potent compound of these series with an $IC_{50}$ value lower than 50 µM. The azide analog 88 showed a three-fold decrease in activity, which supports an interaction of the 4-amino substituent in 87 with the enzyme. The stereochemistry of analog 87 is important for its activity. The introduction of D-Arg$^{NO2}$ in 89 instead of L-Arg$^{NO2}$ decreased the activity two fold. The inversion of configuration at the Cα position in 87 caused a two fold decreased activity (see compound 85). Interestingly, compound 84, containing a D-Arg$^{NO2}$ and a D-proline, showed the same activity as 87 at 100 µM. The activity of the azido dipeptide analog 90 is difficult to explain since its 4-amino analog 89 is two times less potent.

TABLE 4 nNOS activities of the dipeptide analogs containing proline derivatives at the N-terminus.

|  | Activity @ 100 µM | Activity @ 50 µM |
|---|---|---|
| 62 L-cis-Pro$^{4NH2}$-L-Arg$^{NO2}$-NH$_2$ | 48% |  |
| 84 L-cis-Pro$^{4NH2}$-D-Arg$^{NO2}$-NH$_2$ | 24% | 43% |
| 85 D-cis-Pro$^{4NH2}$-L-Arg$^{NO2}$-NH$_2$ | 42% |  |
| 86 D-cis-Pro$^{4NH2}$-D-Arg$^{NO2}$-NH$_2$ | 54% |  |
| 87 L-trans-Pro$^{4NH2}$-L-Arg$^{NO2}$-NH$_2$ | 24% | 34% |
| 88 L-trans-Pro$^{4N3}$-L-Arg$^{NO2}$-NH$_2$ | 67% |  |
| 89 L-trans-Pro$^{4NH2}$-D-Arg$^{NO2}$-NH$_2$ | 47% |  |
| 90 L-trans-Pro$^{4N3}$-D-Arg$^{NO2}$-NH$_2$ | 25% |  |
| 91 D-trans-Pro$^{4NH2}$-L-Arg$^{NO2}$-NH$_2$ | 35% |  |
| 92 D-trans-Pro$^{4N3}$-L-Arg$^{NO2}$-NH$_2$ | 39% |  |
| 93 D-trans-Pro$^{4NH2}$-D-Arg$^{NO2}$-NH$_2$ | 55% |  |
| 94 D-trans-Pro$^{4N3}$-D-Arg$^{NO2}$-NH$_2$ | 50% |  |

Example 47

Figure 18:
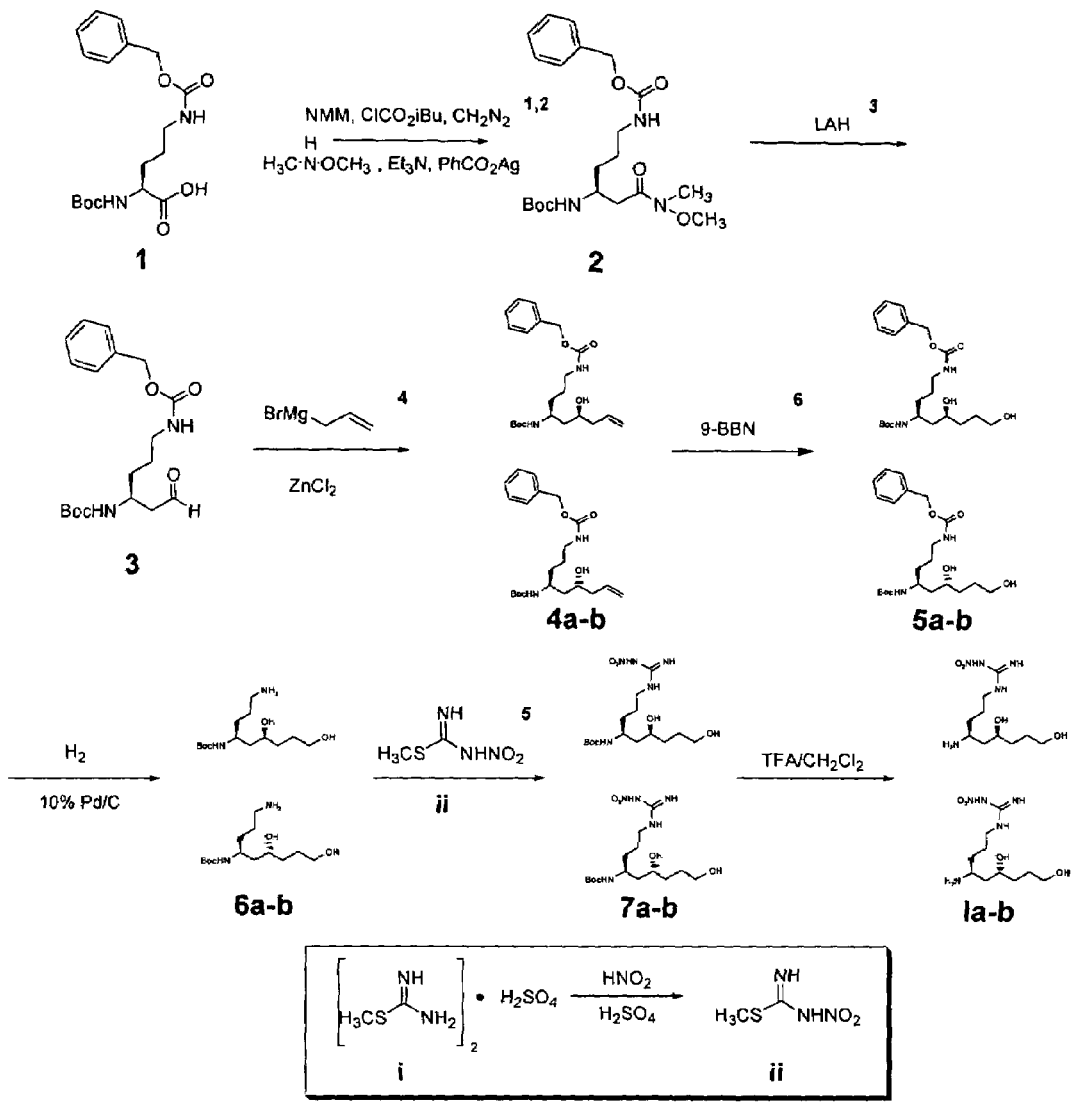

With reference to FIGS. 18 and 22, and enantiomers E1- and E2-propyl-OH, consider examples 47a-47g.

Example 47a

To a flamed dried 250 ml flask charged with argon, was added N,O-dimethyl hydroxylamine hydrochloride (1.60 g, 16.4 mmol) in 20 mL dry THF. Triethylamine (3.04 mL, 26.8 mmol) was added dropwise at room temperature, and the mixture was allowed to stir overnight. The resulting white, Weinreb Amide (2), precipitated salt was filtered off and washed with dry THF.

To a solution of Boc-L-Orn(Z)-OH (1) (4.0 g, 10.9 mmol) in ethylene glycol dimethyl ether (DME) (10 mL), cooled to −20° C. and under argon atmosphere, was added with vigorous stirring 4-methylmorpholine (1.27 mL, 11.4 mmol) followed by isobutylchloroformate (1.56 mL, 12.0 mmol). The resulting white precipitated salt was filtered and washed with DME. The filtrate was added to a batch of diazomethane in ether (~16 mmol). Diazomethane was generated using an Aldrich Diazald Kit, procedures provided. The solution was allowed to stir for 1-2 hours at 0° C., and concentrated in vacuo. The resulting residue was dissolved in dry THF (~50 mL). To this solution, was added the filtrate resulting from the previous reaction followed by silver benzoate (0.51 g, 2.20 mmol) in triethylamine (5.8 mL), and the reaction was allowed to stir overnight. The above reaction was performed in duplicate, and the solutions were combined at this point and worked up as one reaction. The resulting dark brown solution was concentrated in vacuo, and the residue was dissolved in ethyl acetate. The insoluble material was removed by filtration through a pad of Celite. The filtrate was washed with saturated sodium bicarbonate (3×100 mL), water (100 mL), 1 M potassium bisulfite (2×50 mL), brine, dried over anhydrous magnesium sulfate, and concentrated in vacuo. The resulting clear, yellow oil was purified by flash chromatography, (ethyl acetate-hexane 2:1) to afford a clear colorless oil, (6.15 g, 67%).

Example 47b

Beta-aldehyde (3)

A 250 mL three-necked round bottom flask was equipped with a thermometer, flame dried, and charged with argon and a 1 M solution of lithium aluminum hydride in THF (29 mL, 29 mmol). To this solution was added a solution of Weinreb amide (2) in THF (30 mL) dropwise by canular while keeping the temperature below −60° C. After full addition the Dry Ice bath was removed, and the solution was allowed to stir for 30 minutes or until all starting material was consumed. The ice bath was replaced and the reaction was cautiously quenched with saturated potassium bisulfate (10 mL). The ice bath was removed once again, and the solution was allowed to warm to room temperature over 2 hours, resulting in a clear, yellow solution with a white precipitate. The precipitate was removed by filtration through a pad of Celite, and the filtrate was concentrated in vacuo. The resulting residue was dissolved in ethyl acetate and washed with cold 1 N HCl (3×50 mL), saturated sodium bicarbonate (2×50 mL), brine, dried over anhydrous magnesium sulfate, and concentrated in vacuo. The resulting yellow oil was purified by flash chromatography, (hexane-ethyl acetate 3:1) to afford a clear colorless oil that crystallizes under vacuum (2.05 g, 38%).

Example 47c

Allyl Grignard (4a-b)

A three-necked 250 mL round bottom was equipped with a thermometer, flame dried, and charged with argon. To a stirred 1 M solution of Zinc Chloride in ether (16 mL, 16 mmol), was added 40 mL THF. The solution was cooled to 0° C., and a 1 M solution of allylmagnesium bromide was added (24 mL, 24 mmol). After stirring for 30 minutes, the suspension was cooled to −30° C. and a solution of aldehyde (3) in THF (30 mL) was added slowly keeping the internal temperature below −20° C. The reaction was stirred and allowed to warm to room temperature overnight. The mixture was then cooled to −30° C. and cautiously quenched with 100 mL 5% citric acid, and diluted with 200 mL ethyl acetate. The resulting organic layer was washed with water (50 mL), saturated sodium bicarbonate (50 mL), dried over anhyrdrous magnesium sulfate, and concentrated in vacuo. The resulting cloudy oil was purified by flash chromatography (hexane-ethyl acetate 4:1) to afford two separate diastereomers as clear, colorless oils (1.0 g, 44% and 0.72 g, 32%; 76% total). The two diastereomers were separated, but the absolute stereochemistry of each is yet to be determined. The following procedures were completed using both isomers, but one example procedure is given for each.

Example 47d

Propyl Alcohol (BBN) (5a-b)

A sample of allyl alcohol (4) (0.12 g, 0.29 mmol) was added to a 50 mL round bottom flask, dried overnight using a vacuum pump, and charged with argon. To this sample, was added a 0.5 M solution of 9-BBN in THF (5.8 mL, 2.9 mmol)

at room temperature, and the reaction was allowed to stir overnight. The mixture was then cooled to 0° C. and 2 M potassium hydroxide (5 mL, 10 mmol) was added, followed by 5 mL of 30% hydrogen peroxide. After stirring for 5 minutes, the solution was diluted with ethyl acetate (25 mL), washed with water (3×50 mL) and brine, dried over anhydrous magnesium sulfate, and concentrated in vacuo. The cloudy oil was purified by flash chromatography (methylene chloride-methanol 50:1) to afford a clear, colorless oil (35 mg, 29%). This procedure is one representative sample of this reaction. This procedure was repeated for both isomers.

Example 47e

Propyl Alcohol Product (6a-b)

To a 25 mL round bottom flask was added Cbz-protected alcohol (5) (0.035 g, 0.082 mmol), which was dissolved in methanol (10 mL). To this solution was added 10% Pd/C (10 mg), and the suspension was exposed to hydrogen gas overnight. The suspension was then filtered through a pad of Celite and concentrated in vacuo to afford a yellow oil. The crude yellow oil was used in the next reaction without purification. This procedure is one representative sample of this reaction. This procedure was repeated for both isomers.

Example 47f $Arg^{NO2}$ Propyl Alcohol Product (7a-b)

To a solution of the crude amine (6) (0.23 g, 0.082 mmol) in absolute ethanol (5 mL), was added N-nitromethylthioguanidine (0.012 g, 0.091 mmol), the solution was heated at 40° C. for 5 minutes and allowed to stir overnight at room temperature. The reaction mixture was concentrated in vacuo, and purified by flash chromatography (ethyl acetate-hexane 7:1) to afford a clear, colorless oil (0.025 g, 81%). This procedure is one representative sample of this reaction. This procedure was repeated for both isomers.

Example 47g $Arg^{NO2}$ Propyl Alcohol Final Product (Ia-b)

Boc-protected nitroarginine propyl alcohol (7) (0.025 g, 0.066 mmol) was dissolved in 50% TFA in methylene chloride, and allowed to stir for 3 hours at room temperature. The mixture was concentrated in vacuo, and the resulting yellow oil was dissolved in ethanol. Concentrated HCl was added dropwise until the solution became cloudy, and the solution was concentrated once again. The resulting yellow oil was purified by HPLC to afford a white powder (0.02 g, 99%). This procedure is one representative sample of this reaction. This procedure was repeated for both isomers.

Example 48

Figure 19:
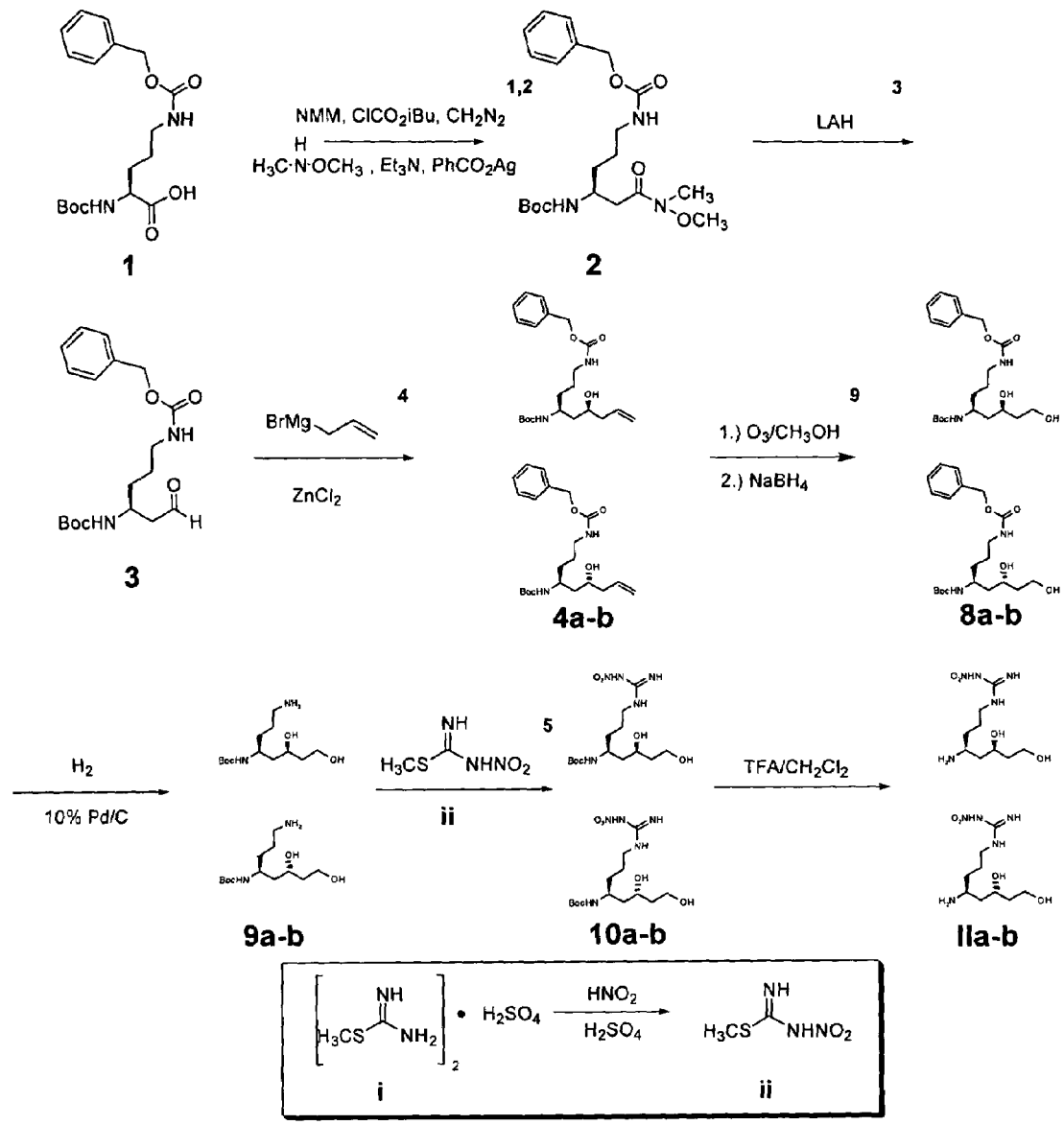

With reference to FIGS. 19 and 22, and enantiomers E1- and E2-ethyl-OH, consider examples 48a-48d.

Example 48a CBz-Protected Ethyl Alcohol (8a-b)

To a 100 ml three-necked round bottom flask, was added a solution of allyl alcohol (4) (0.30 g, 0.74 mmol) in methanol (10 mL). Ozone was bubbled through the solution at a constant rate for 1-2 hours or until all starting material was consumed. The reaction was then worked up by the addition of sodium borohydride (0.28 g, 7.4 mmol). After stirring for several hours, the mixture was concentrated in vacuo and the resulting residue was dissolved in ethyl acetate. The solution was then washed with saturated ammonium chloride, brine, dried over anhydrous magnesium sulfate, and concentrated in vacuo to afford a cloudy oil. The oil was purified by flash chromatography (methylene chloride-methanol 50:1) to afford a clear, colorless oil (0.15 g, 49%). This procedure is one representative sample of this reaction. This procedure was repeated for both isomers.

Example 48b

Ethyl Alcohol Product (9a-b)

To solution of (8) (0.050 g, 0.12 mmol) in methanol (10 mL), was added Pd/C (0.050 g). The suspension was exposed to hydrogen gas and allowed to stir overnight. The suspension was then filtered through a pad of Celite and concentrated in vacuo to afford a yellow oil. The crude yellow oil was used in the next reaction without purification. This procedure is one representative sample of this reaction. This procedure was repeated for both isomers.

Example 48c $Arg^{NO2}$ Ethyl Alcohol Product (10a-b)

To a solution of the crude alcohol (9) in absolute ethanol (5 mL), was added N-nitromethylthioguanidine (16 mg, 0.12 mmol), the solution was heated at 40° C. for 5 minutes and allowed to stir overnight at room temperature. The reaction mixture was concentrated in vacuo, and purified by flash chromatography (ethyl acetate-hexane 7:1) to afford a clear, colorless oil (20 mg, 46%). This procedure is one representative sample of this reaction. This procedure was repeated for both isomers.

Example 48d $Arg^{NO2}$ Ethyl Alcohol Final Product (IIa-b)

Boc-protected nitroarginine ethyl alcohol (10) (0.021 g, 0.058 mmol) was dissolved in 50% TFA in methylene chloride, and allowed to stir for 3 hours at room temperature. The mixture was concentrated in vacuo, and the resulting yellow oil was dissolved in ethanol. Concentrated HCl was added dropwise until the solution became cloudy, and the solution was concentrated once again. The resulting yellow oil was purified by HPLC to afford a white powder (0.017 g, 99%). This procedure is one representative sample of this reaction. This procedure was repeated for both isomers.

Example 49

Figure 20:
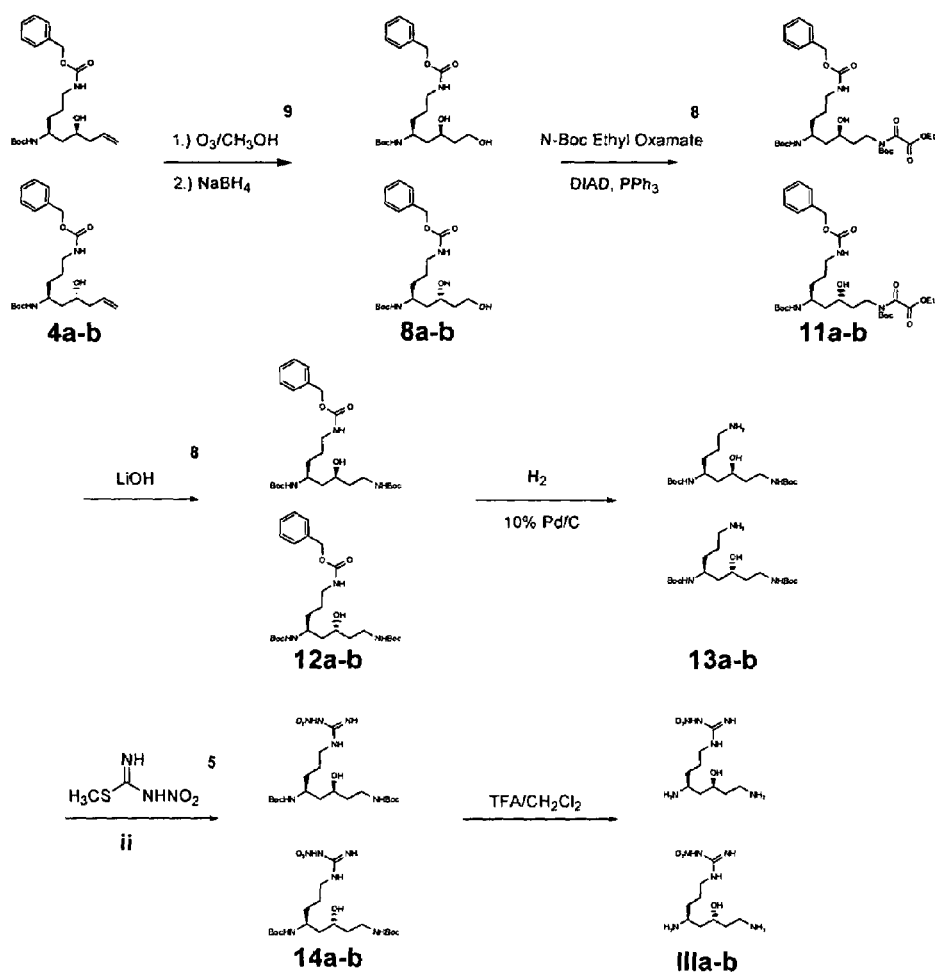

With reference to FIGS. 20 and 22, and enantiomers E1- and E2-ethyl-$NH_2$, consider examples 49a-49e.

Example 49a

CBz-Protected Ethyl Alcohol Mitsunobu (11a-b)

A two-necked 100 mL round bottom flask was equipped with a water-jacketed condenser, flame dried, and placed under argon atmosphere. Triphenylphosphine (0.070 g, 0.26 mmol) and N-Boc-ethyl-oxamate (0.059 g, 0.26 mmol) were added, followed by a solution of the Cbz-protected ethyl alcohol (8) (0.10 g, 0.24 mmol) in dry THF (5 mL). The solution was cooled to 0° C., and diisopropyl azodicarboxylate (0.053 mL, 0.26 mmol) was added dropwise. The reaction was then heated to 60° C., and allowed to stir overnight. The resulting light yellow liquid was concentrated in vacuo, and purified by flash chromatography (hexane-ethyl acetate 5:1) to afford a clear, colorless oil (0.050 g, 31%). This procedure is one representative sample of this reaction. This procedure was repeated for both isomers.

Example 49b

Cbz-Orn Ethyl Amine Product (12a-b)

To a solution of the oxamate (11) (0.05 g, 0.08 mmol) in THF (4 mL), a solution of lithium hydroxide (0.14 g, 6 mmol) in water (3 mL) was added at room temperature. After 3 hours, the reaction mixture was diluted with water and extracted with methylene chloride. The organic layer was dried over anhydrous sodium sulfate, and concentrated in vacuo. The resulting cloudy oil was purified by flash chromatography (hexane-ethyl acetate 1:1) to afford a clear, colorless oil (0.04 g, 98%). This procedure is one representative sample of this reaction. This procedure was repeated for both isomers.

Example 49c

Ethyl Amine Product (13a-b)

To solution of (12) (0.050 g, 0.10 mmol) in methanol (10 mL), was added Pd/C (0.050 g). The suspension was exposed to hydrogen gas and allowed to stir overnight. The suspension was then filtered through a pad of Celite and concentrated in vacuo to afford a yellow oil. The crude yellow oil was used in the next reaction without purification. This procedure is one representative sample of this reaction. This procedure was repeated for both isomers.

Example 49d

Arg$^{NO2}$ Ethyl Amine Product (14a-b)

To a solution of the crude amine (13) in absolute ethanol (5 mL), was added N-nitromethylthioguanidine (13 mg, 0.10 mmol), the solution was heated at 40° C. for 5 minutes and allowed to stir overnight at room temperature. The reaction mixture was concentrated in vacuo, and purified by flash chromatography (ethyl acetate-hexane 7:1) to afford a clear, colorless oil (15 mg, 32%). This procedure is one representative sample of this reaction. This procedure was repeated for both isomers.

Example 49e

Arg$^{NO2}$ Ethyl Amine Final Product (IIIa-b)

Boc-protected nitroarginine ethyl amine (14) (0.015 g, 0.032 mmol) was dissolved in 50% TFA in methylene chloride, and allowed to stir for 3 hours at room temperature. The mixture was concentrated in vacuo, and the resulting yellow oil was dissolved in ethanol. Concentrated HCl was added dropwise until the solution became cloudy, and the solution was concentrated once again. The resulting yellow oil was purified by HPLC to afford a white powder (0.010 g, 99%). This procedure is one representative sample of this reaction. This procedure was repeated for both isomers.

Example 50

Figure 21:
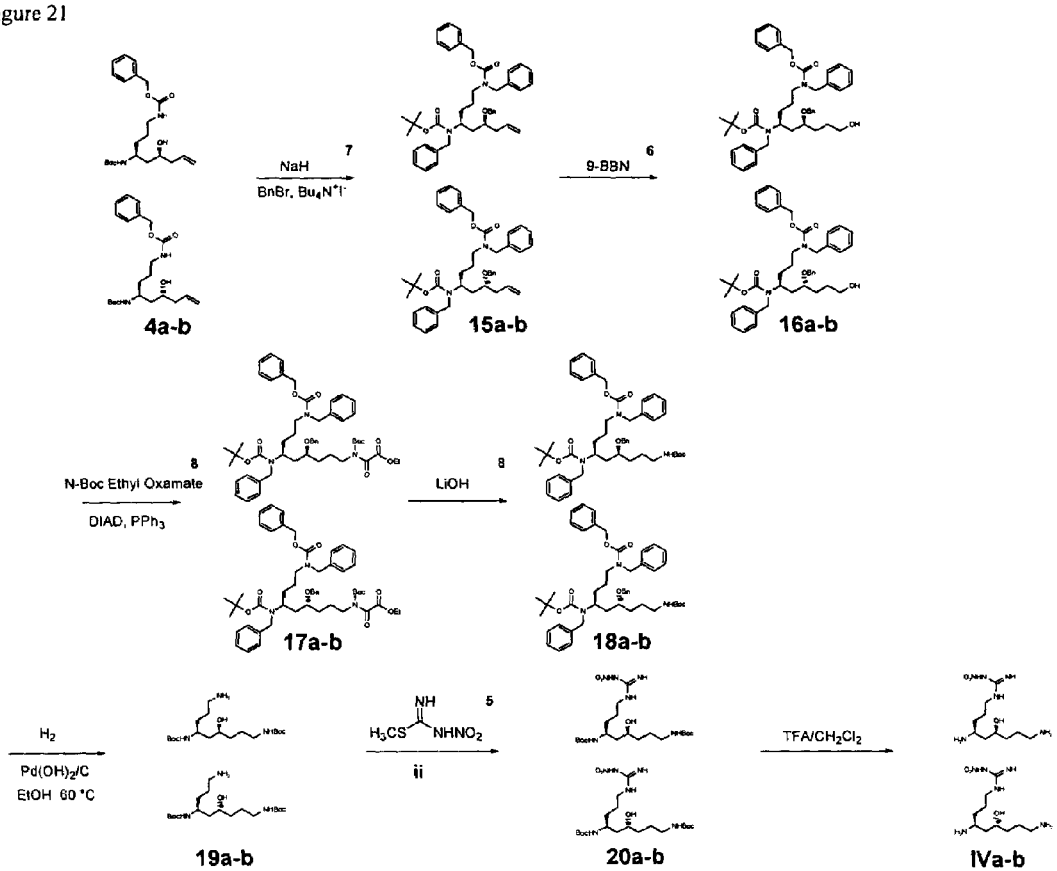

With reference to FIGS. 21 and 22, and enantiomers E1- and E2-propyl-NH$_2$, consider examples 50a-50g Example 50a Tribenzyl Product (15a-b)

To a 100 mL round bottom flask, flame dried and charged with argon, was added allyl alcohol (4) (0.63 g, 1.55 mmol). The oil was dissolved in anhydrous DMF (10 mL), and treated with 60% sodium hydride in mineral oil (0.62 g, 15.5 mmol). The suspension was cooled to 0° C., followed by addition of tetrabutylammonium iodide (1.91 g, 5.17 mmol) and benzyl bromide (0.61 mL, 5.17 mmol). The mixture was allowed to warm to room temperature overnight, cooled to 0° C., and cautiously quenched with saturated ammonium chloride. The solution was extracted with methylene chloride (3×50 mL), and the combined organic layers were concentrated in vacuo to afford a clear oil white solid mixture. The mixture was dissolved in methylene chloride and was purified by flash chromatography (hexane-ethyl acetate 6:1) to afford a clear, colorless oil (0.46 g, 44%). This procedure is one representative sample of this reaction. This procedure was repeated for both isomers.

Example 50b

Tribenzyl Product Alcohol (16a-b)

To a 100 mL round bottom flask, flame dried and charged with argon, was added tribenzyl product (15) (0.46 g, 0.68 mmol). The oil was then dissolved in a 0.5 M solution of 9-BBN in THF (13.6 mL, 6.8 mmol), and allowed to stir at room temperature overnight. The flask was cooled to 0° C. and 2.0 M aqueous KOH (10 mL, 20 mmol) was added, followed by 30% hydrogen peroxide (10 mL). After stirring for 5 minutes, the solution was diluted using ethyl acetate (50 mL). The resulting organic layer was washed with water (5×50 mL) and brine, and concentrated in vacuo to afford a white, cloudy oil. The crude product was purified by flash chromatography (methylene chloride-methanol 40:1). Some impurities remained, so the crude material was purified by flash chromatography a second time (hexane-ethyl acetate 3:1) to afford a soap-like white solid (0.39 g, 82%). This procedure is one representative sample of this reaction. This procedure was repeated for both isomers.

Example 50c

Tribenzyl Mitsunobu Product (17a-b)

A two-necked 100 mL round bottom flask was equipped with a water-jacketed condenser, flame dried, and placed under argon atmosphere. Triphenylphosphine (0.16 g, 0.62 mmol) and N-Boc-ethyl-oxamate (0.14 g, 0.62 mmol) were added, followed by a solution of the tribenzyl alcohol (16) (0.39 g, 0.56 mmol) in dry THF (10 mL). The solution was cooled to 0° C., and diisopropyl azodicarboxylate (0.12 mL, 0.62 mmol) was added dropwise. The reaction was then heated to 60° C., and allowed to stir overnight. The resulting light yellow liquid was concentrated in vacuo, and purified by flash chromatography (hexane-ethyl acetate 7:1) to afford a clear, colorless oil (0.24 g, 48%). This procedure is one representative sample of this reaction. This procedure was repeated for both isomers.

Example 50d

Boc-protected Product (18a-b)

To a solution of the oxamate (17) (0.50 g, 0.56 mmol) in THF (4 mL), a solution of lithium hydroxide (0.14 g, 6.0 mmol) in water (3 mL) was added at room temperature. After 3 hours, the reaction mixture was diluted with water and extracted with methylene chloride. The organic layer was dried over anhydrous sodium sulfate, and concentrated in vacuo. The resulting cloudy oil was purified by flash chromatography (hexane-ethyl acetate 1:1) to afford a clear, colorless oil (0.40 g, 90%). This procedure is one representative sample of this reaction. This procedure was repeated for both isomers.

Example 50e

Propyl Amine Product (19a-b)

To solution of (18) (1.01 g, 1.27 mmol) in ethanol (50 mL), was added Pd(OH)$_2$/C (0.25 g). The suspension was exposed to hydrogen gas, heated to 60° C., and allowed to stir overnight. The suspension was then filtered through a pad of Celite and concentrated in vacuo to afford a yellow oil. The crude yellow oil was used in the next reaction without purification. This procedure is one representative sample of this reaction. This procedure was repeated for both isomers.

Example 50f

Arg$^{NO2}$ Propyl Amine Product (20a-b)

To a solution of the crude amine (19) in absolute ethanol (20 mL), was added N-nitromethylthioguanidine (0.17 g, 1.27 mmol) and triethylamine (1 mL), the solution was heated at 40° C. for 5 minutes and allowed to stir overnight at room temperature. The reaction mixture was concentrated in vacuo, and purified by flash chromatography (ethyl acetate-hexane 7:1) to afford a clear, colorless oil (0.20 g, 33%). This procedure is one representative sample of this reaction. This procedure was repeated for both isomers.

Example 50g

Arg$^{NO2}$ Propyl Amine Final Product (IVa-b)

Boc-protected nitroarginine propyl amine (20) (0.050 g, 0.10 mmol) was dissolved in 50% TFA in methylene chloride, and allowed to stir for 3 hours at room temperature. The mixture was concentrated in vacuo, and the resulting yellow oil was dissolved in ethanol. Concentrated HCl was added dropwise until the solution became cloudy, and the solution was concentrated once again. The resulting yellow oil was purified by HPLC to afford a white powder (0.036 g, 99%). This procedure is one representative sample of this reaction. This procedure was repeated for both isomers.

While the principles of this invention have been described in connection with specific embodiments, it should be understood clearly that these descriptions are added only by way of example and are not intended to limit, in any way, the scope of this invention. For instance, numerous compositions of this invention have been prepared and/or described as salts thereof, but can also be provided as would otherwise be known to those skilled in the art for purposes of bioavailability or increased effectiveness. Likewise, this invention includes various other N-nitroguanidinyl and/or N-nitroargininyl compounds of the type described herein, such compounds as can be prepared to include a range of structural or functional substituents and/or other N- or C-terminus substituents, as would also be understood by those skilled in the art made aware of this invention, depending upon choice of reagent(s) or reaction conditions, using known synthetic techniques and/or straight-forward modifications of the procedures described herein. Other advantages, features and benefits will become apparent from the claims to be filed hereafter, with the scope of such claims determined by their reasonable equivalents, as would be understood by those skilled in the art.

We claim:

1. A peptidomimetic compound of a formula

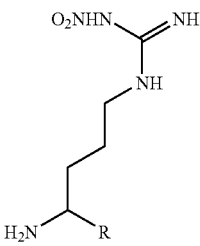

wherein R is selected from CH$_2$CH(OH)(CH$_2$)$_n$X moieties, where n is an integer ranging from 1 to about 3, and X is selected from hydroxy and amino groups.

2. The compound of claim 1 wherein X is hydroxy.
3. The compound of claim 1 wherein X is amino.
4. The compound of claim 1 selected from

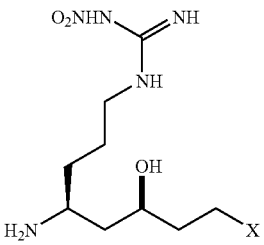

or

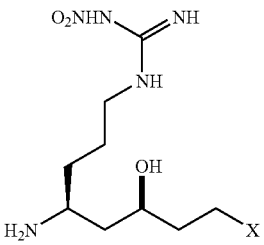

\* \* \* \* \*

UNITED STATES PATENT AND TRADEMARK OFFICE
CERTIFICATE OF CORRECTION

PATENT NO. : 7,470,815 B1 Page 1 of 1
APPLICATION NO. : 11/341404
DATED : December 30, 2008
INVENTOR(S) : Richard B. Silverman et al.

It is certified that error appears in the above-identified patent and that said Letters Patent is hereby corrected as shown below:

Title Page, Priority Data (missing) should be inserted

--(60) Related U.S. Application Data
This application is a CIP of 10/963,416, filed 10/12/2004 ABN
which is a CON of 10/178,625 06/24/2002 PAT 6,803,486
which claims benefit of 60/300,130 06/22/2001
and claims benefit of 60/315,587 08/29/2001--

Signed and Sealed this

Twenty-sixth Day of January, 2010

David J. Kappos
*Director of the United States Patent and Trademark Office*